(12) United States Patent
Cahoon et al.

(10) Patent No.: US 7,271,317 B2
(45) Date of Patent: Sep. 18, 2007

(54) PHYTIC ACID BIOSYNTHETIC ENZYMES

(75) Inventors: Rebecca E. Cahoon, Webster Groves, MO (US); William D. Hitz, Wilmington, DE (US); Richard W. Pearlstein, Newark, DE (US); Thomas J. Carlson, San Diego, CA (US)

(73) Assignee: E. I. du Pont de Nemours and Company, Wilminton, DE (US)

( * ) Notice: Subject to any disclaimer, the term of this patent is extended or adjusted under 35 U.S.C. 154(b) by 185 days.

(21) Appl. No.: 11/038,329

(22) Filed: Jan. 18, 2005

(65) Prior Publication Data

US 2005/0164269 A1   Jul. 28, 2005

Related U.S. Application Data

(60) Division of application No. 10/324,316, filed on Dec. 20, 2002, now Pat. No. 6,855,869, which is a continuation of application No. 09/686,521, filed on Oct. 11, 2000, now abandoned, which is a continuation of application No. PCT/US99/08790, filed on Apr. 22, 1999.

(60) Provisional application No. 60/082,960, filed on Apr. 24, 1998.

(51) Int. Cl.
  *A01H 1/00* (2006.01)
  *C07H 21/04* (2006.01)
  *C07K 14/415* (2006.01)
  *C12N 5/14* (2006.01)
  *C12N 9/00* (2006.01)

(52) U.S. Cl. .................... 800/295; 435/6; 435/69.1; 435/468; 435/419; 435/252.3; 435/320.1; 435/183; 530/370; 536/23.6; 800/278

(58) Field of Classification Search .............. 435/6, 435/69.1, 468, 419, 252.3, 320.1, 183; 530/370, 530/23.6; 800/278, 296
See application file for complete search history.

(56) References Cited

U.S. PATENT DOCUMENTS 5,593,963 A   1/1997   Van Ooijen et al.

FOREIGN PATENT DOCUMENTS

| WO | WO91/14782 | 10/1991 |
|---|---|---|
| WO | WO98/05785 | 2/1998 |
| WO | WO99/05298 | 2/1999 |
| WO | WO99/07211 | 2/1999 |

OTHER PUBLICATIONS

Barbara F. Harland et al., J. Assoc. Off. Anal. Chem., vol. 69(4):667-670, 1986, Anion-Exchange Method for Determination of Phytate in Foods: Collaborative Study.
Jean-Claude Pernollet, Phytochemistry, vol. 17:1473-1480, 1978, Protein Bodies of Seeds: Ultrastructure, Biochemistry, Biosynthesis and Degradation.
Boyd L. O'Dell et al., J. Agr. Food Chem., vol. 20(3):718-721, 1972, Distribution of Phytate and Nutritionally Important Elements among the Morphological Components of Cereal Grains.
Z. Mroz et al., J. Animal Science, vol. 72:126-132, 1994, Apparent Disgestibility and Retention of Nutrients Bound to Phytate Complexes as Influenced by Microbial Phytase and Feeding Regimen in Pigs.
M. R. Spivey Fox et al., In Nutritional Toxicology, vol. 3, Academic Press, San Diego (1989) pp. 59-96, Antinutritive Effects of Phytate and Other Phosphorylated Derivatives.
Victor Raboy, Inositiol Metabolism in Plants, (1990) Wiley-Liss, New York, pp. 55-76, Biochemistry and Genetics of Phytic Acid Synthesis.
Jan Pen et al., Bio/Technology, vol. 11, Jul. 1993, 811-814, Phytase-containing Transgenic Seeds as a Novel Feed Additive for Improved Phosphorus Utilization.
Glenda E. Gillaspy et al., The Plant Cell, vol. 7:2175-2185, Dec. 1995, Plant Inositiol Monophosphatase is a Lithium-sensitive Enzyme Encoded by a Multigene Family.
EMBL Sequence Library Data Accession No. D47093, Mar. 9, 1995, Sasaki, T. et al., Rice cDNA from shoot.
EMBL Sequence Library Data Accession No. C72860, Sep. 19, 1997, Sasaki, T. et al., Rice cDNA from panicle at flowering stage.
Monita P. Wilson et al., Biochem. & biophys. Res. Comm.,, vol. 232:678-681, 1997, Characterization of a cDNA encoding *Arabidopsis thaliana* Inositol 1,3,4-trisphosphate 5/6-kinase.
Jia Li et al., Plant Phys., vol. 114:1103-1111, 1997, Secretion of Active Recombinant Phytase from Soybean Cell-Suspensioin Cultures.
Francisco J. Quintero et al., Plant cell, vol. 8:529-537, 1996, The SAL1 Gene of *Arabidopsis*, encoding an enzyme with 3'(2'),5'-Bisophosphate nucleotidease and Inositol Polyphosphate 1-Phosphatase Activities, increases salt tolerance in yeast.
Akio Matsuhisa et al., Journ. of Bacteriology, vol. 177(1):200-205, 1995, Inositol Monophosphatase Activity from the *Escherichia coli* suhB gene product.
Gillaspy, Glenda, Plant Phys., vol. 114(3) suppl:314, 1997, Transgenic reduction of inositol monophosphatase disrupts vegetative development, XP-002112476.
National Center for Biotechnology Information General Identifier No. 3660465, Sep. 25, 1998, Xue, H.
Bork, Genome Research, vol. 10:398-400, 2000.
Lazar et al., Molecular and Cellular Biology, vol. 8(3):1247-1252, 1988.
Burgess et al., The Journal of Cell Biology, vol. 111:2129-2138, 1990.
Broun et al., Science, vol. 282:131-133, 1998.
N_Geneseq Database, Accession No. AAX24403, Martino-Catt et al., WO9905298, Feb.4, 1999.

*Primary Examiner*—Phuong T. Bui

(57) ABSTRACT

This invention relates to an isolated nucleic acid fragment encoding a phytic acid biosynthetic enzyme. The invention also relates to the construction of a chimeric gene encoding all or a portion of the phytic acid biosynthetic enzyme, in sense or antisense orientation, wherein expression of the chimeric gene results in production of altered levels of the phytic acid biosynthetic enzyme in a transformed host cell.

10 Claims, 5 Drawing Sheets

Figure 1A

```
                                1                                                               60
SEQ ID NO:33 (gi 3396079)       ------------------------------------------------------MSDSI--
SEQ ID NO:34 (gi 3660465)       ------------------------------------------------------MSDSI--
SEQ ID NO:2                     ------------------------------MRLHAEVRDEMEEGSEVGAVTASAGLSPPPLIGA
SEQ ID NO:4                     ------MPQ-------FVEKTDLPR-------------------------------------
SEQ ID NO:6                     --------------------------------------------------------------
SEQ ID NO:8                     --------------------------------------------------MASDAAAEPSSGV
SEQ ID NO:10                    --------------------------------------------------------------
SEQ ID NO:12                    -------------------------------------------------MAGD---EPLPGD
SEQ ID NO:14                    MA-------------------------------------------P--------ELSSPS--
SEQ ID NO:16                    AIYIPTFPISLLSFLFLSLTHPFRWPRIPITIGPSTPLPLSPKLGFLSGNVIQRAAAS
SEQ ID NO:18                    ------------------------------MRLNGELSSGEEEEKQTGTTPS--------
SEQ ID NO:20                    ------------------------------------------------------------H
SEQ ID NO:22                    --------------------------------------------------------------
SEQ ID NO:24                    MV-------------------------------------H---------------DHQS-G--
SEQ ID NO:26                    I-------------------------------------A-----------------------
SEQ ID NO:28                    --------------------------------------------------------------
SEQ ID NO:30                    --------------------------------------------------------------
SEQ ID NO:32                    --------------------------------------------------------------

61                                                              120
SEQ ID NO:33 (gi 3396079)       --QERY-LVGYALAAKKQHSFIQPSLIEHSRQRGIDLVKLDPTKSLLEQGKLDCIIHKLY
SEQ ID NO:34 (gi 3660465)       --QERY-LVGYALAAKKQHSFIQPSLIEHSRQRGIDLVKLQPTKSLLEQGKLDCIIHKLY
SEQ ID NO:2                     AAPVPRIVWGFALTKKVKSFLQPKLLLAKKNGTSFVSIDESLPLSEQGPFDXILEXIT
SEQ ID NO:4                     ----VGYALPKRKIRAFMVESFINYAKERKIDFIPIDVSKPLTEQGPFNCIHKMY
SEQ ID NO:6                     THPPRY-VIGYALPKKQQSFIQPSLVAQAASRGMDLVPVTDASQPLAEQGPFHLLIHKLY
SEQ ID NO:8                     GQRRRY-LIGYALAPKKQQSFIQPSLIEHSRQRGIDLVKLDPTKSILLEQGPFHLLIHKLY
SEQ ID NO:10                    --SSPRYTVGYALLPEKVSSVVRPSLVALAADRGVRLVAVDVSRPLAEQGPFDLLVHKMY
SEQ ID NO:12                    AAEKREGVIGYALAPKKQNSFIRDSLVSLAKSRGIELVRVDSDKPLADQGPFDCVLHKLY
SEQ ID NO:14                    MAEKREGVIGYALAPKKQNSFIRDSLVSLAKSRGIELVRVDSDKPLADQGPFDCVLHKLY
SEQ ID NO:16                    ---BQKVVVGYALTSKKKKKSFLQPSFTGLARNRGINFVAIDINKPLLEQGPFDIIIHKLS
SEQ ID NO:18                    QAGQRY-RVGYALQGKKVESFIQPSLLDHAKQESIDLVQIDPTAPLQQQGPFHCIIHKLH
SEQ ID NO:20                    --PRPRVTIGYALPPGKAGSVIQPPLERLAAERGMRLVAVDASLPLADQGPFDLIIHKLF
SEQ ID NO:22                    -----------------------------------------------SSRPALDKG----
SEQ ID NO:24                    -------------------------------------------EDQGPFDVILHKLT
SEQ ID NO:26                    --------------------------------------------------------------
SEQ ID NO:28                    --------------------------------------------------------------
SEQ ID NO:30                    --------------------------------------------------------------
SEQ ID NO:32                    --------------------FIPIDETRPLSEQGPFDIILHKT
```

Figure 1B

```
                                121                                                                                 180
SEQ ID NO:33 (gi 3396079)   DV-------------YWKENLHEFREKCPGVPVI-DLPEAIERLHNR----VSNLEVITQL
SEQ ID NO:34 (gi 3660465)   DV-------------YWKENLHEFREKCPGVPVI-DLPEAIERLHNR----VSMLEVITQL
SEQ ID NO:2                 RK-------------EWQKVLKKYXEEHPEVTKL-DPPNAIEHLNNR----QSMLEVADL
SEQ ID NO:4                 GQ-------------EWNQNLESFINNPNATVI-DQPTSIQRLHNR----ISMLEPVTQL
SEQ ID NO:6                 ---------------HRPNVTVL-DPPDAIQHVHNR----QSMLQDVADL
SEQ ID NO:8                 GD-------------DWRAQLVAFAARQFKVPSS-TRPRH-RPLHNR----ISMLQVVSEL
SEQ ID NO:10                ---------------EHPEVTVL-DPPGAIEHLLNR----QSMLQEVSEL
SEQ ID NO:12                GE-------------ENRGQLDAFSAAHPAVPVV-DPPHAIDRLHNR----ISMLQVVSEL
SEQ ID NO:14                DR-------------GWRAQLEELAARHPGVTVVVDSPGAIDRLLDRA----TMLDVVSGL
SEQ ID NO:16                GD-------------DWKRQLQEFHTLYPNWAVIL-DAPEAIERLHNR----ISMLQVVSEL
SEQ ID NO:18                GE-------------EWCBIIEDYROKHPEVTVL-DPPDAIQHLHNR----QSMLQDVVDL
SEQ ID NO:20                ------------------------------------------------
SEQ ID NO:22                TQ-------------HWKNLLQQPSSKPNTVII-DPPELVDRLHNR----VSMLQAVTHL
SEQ ID NO:24                DR-------------PWRAQLBAFSALHPSVPVV-DAPAAVDRILDRF----TMLDVVPGL
SEQ ID NO:26                ------------------------------------------------
SEQ ID NO:28                GK-------------EMQRRLBEYRDTHPEVTVL-DPPGAIEHLLNR----QSMLQEVSKL
SEQ ID NO:30                ------------------------------------------------
SEQ ID NO:32                SK-------------EMQRFLEDYHEVHPEVTVL-DPPNAIEHLNNR----QSMLEEVADL 181                                                                                 240
SEQ ID NO:33 (gi 3396079)   RPFVS--D-SERFGVPEQVVVM-DSSV--LSGGGALGELKFPVIAKPLDADGSAKSHKMF
SEQ ID NO:34 (gi 3660465)   RPFVS--D-SERFGVPEQVVVM-DSSV--LSGGGALGELKFPVIAKPLDADGSAKSHKMF
SEQ ID NO:2                 N-----LSNPYGEVCLPRQLVTK--DPSSIPTSVAMAGLTLPLVAKPLVDGTSKGHELY
SEQ ID NO:4                 NIP-------------------------------------------------------
SEQ ID NO:6                 N----LSDSYGTTGVPKQLVT--KNDPTSIPDAVNKAGLRLPNVAKPLV----AKSHELS
SEQ ID NO:8                 DHAVD--Q-DSTFGIPSQVVVY-DAAA--LADPGLLALRFPLIAKPLVADGTAKSHKMS
SEQ ID NO:10                D-----LSDCHGRVGVPKQLFV--NTDPSSIPAAVMRAGLSLPLVAKPLV----AKSHELS
SEQ ID NO:12                DVPLMAHH-HHTFGIPSQVVVY-DAAA--LSDSGLLAALRFPLIAKPLVADGTAKSHKMS
SEQ ID NO:14                RN-----P---VSWRPQVVVSDAA-ATRTSS----LAARAPLL-----------------
SEQ ID NO:16                RIE-D-R-PETEGIPKQIVLY-DKAI--LLDPQAWESLKFPVIAKPLVADGSAKSHKMA
SEQ ID NO:18                N-----LSDCHGKVGVPRQLVIPKEKDPSSIPYHITKAGMKLPLVAKPLVDGTAKSHELF
SEQ ID NO:20                QFSLR-----NATIGVPKQVVVN--EPKSFDLHKFEEBCGLRFPVIAKPLAADGGAGSHELC
SEQ ID NO:22                AAGLDPP-------LSVPAQVTVKRRRAGRGRP-----STGSLPLIAKPLAS--------
SEQ ID NO:24                ------------------------------------------------
SEQ ID NO:26                D-----LADCHGKVGVPKQLFV--NTDPLSIPAAVMRAGLSLPLVAKPLV----AKSHELS
SEQ ID NO:28                ------------------------------------------------
SEQ ID NO:30                ------------------------------------------------
SEQ ID NO:32                N-----LSSFYEBVCTPRQLVIMK--DPSSIPTAVAMAGLTLPLVAKPLVDGTSKSHELS
```

Figure 1C

```
                              241                                                          300
SEQ ID NO:33 (gi 3396079)  LIYDQEGMKILKAPIVLQEFVHHGGVIFKVYVVGDHVQCVKRRSLPDISBEKI---GTSK
SEQ ID NO:34 (gi 3660465)  LIYDQRGMKILKAPIVLQEFVNHGGVIFKVYVVGDHVRCVKRRSLPDISEEKI---GTSK
SEQ ID NO:2                LAYDEASLSMLDPPLVLQEFINHGGILFKVYIIGETIQVVRRPSLPDVNTYDLLNNV----
SEQ ID NO:4                ------------------------------------------------------------
SEQ ID NO:6                LAYDEFSLQNLEPPLVLQEFINHGGVLFKVYIVGEAIKVVRRFSLPDVSKRELSKNA----
SEQ ID NO:8                LVYHREGLGKLRPPLVLQEFVNHGGVIFKVYVVGGHVTCVKRRSLPDVSPE-D-DASAQ
SEQ ID NO:10               LAYDPISLTKLEPPLVLQEFVNHGGVLFKVLVIVGDAIRVVRRFSLPNVDVGDLSNMA---
SEQ ID NO:12               LVTHREGLRKLRPPLVLQEFVNHGGVIFKVYVVGAHVTCVKRRSLPDVSSDVLQ-DASGB
SEQ ID NO:14               ------------------------------------------------------------
SEQ ID NO:16               LVFTRDALNKLKPPIVLQEFVNHGGVIFKVYVVGEHVRCVKRKSLPDVSDEEKALGGVSE
SEQ ID NO:18               LAYDEFSLSELEPPLVTQEFVNHGGLLFKIYIVGETIKVVKRFSLPNISKHEVSKVA---
SEQ ID NO:20               ------LFKVYIVGDAIKVVRRFSLPNVSKWELSKDA---
SEQ ID NO:22               LVPDEEGLHALSVPMVLQEFVNHGGVVFKIYVAGQRVNCVKRKSLGDITEERLKV---LR
SEQ ID NO:24               ------------------------------------------------------------
SEQ ID NO:26               LAYDSASLITKLEPPLVLQEFVNHGGVLFKVYIVGDAIRVVRRF SLPNV-----
SEQ ID NO:28               ------------------------------------------------------------
SEQ ID NO:30               ------------------------------------------------------------
SEQ ID NO:32               LAYDEASLPWLDPPLVLQEFVNHGGDLFKVYIIGEAIQVVRRFSLPDVKPLALLANNC--

301                                                          360
SEQ ID NO:33 (gi 3396079)  GSLPFSQISNLTAQEDKNIEYGEDRSLEKVENPLSFLTDLAKAMRESMGLNLFMPDVIR
SEQ ID NO:34 (gi 3660465)  GSLPFSQISNLTAQEHDKNIEYGEDRSLEKVEMPLSFLTDLAKAMRESMGLNLFMFDVIR
SEQ ID NO:2                GIYRLPRVSCAAASADDADLDPLI------AELPPRPLLEKLGRELRGREFGLRLFNIDMIR
SEQ ID NO:4                ------------------------------------------------------------
SEQ ID NO:6                GVTRFPRVSCAAASADEADLDPCV------AELPPRPLLEKIARNLRHRLGLRLRLFVLDVIR
SEQ ID NO:8                GSVSFSQVSNLPTERTAREYYGEKS-LEDAVVPPAAFTNQIAGGKPRALGLQLFNPDMIR
SEQ ID NO:10               GVFRFPRVSCASANADDADLDPHV------AELPRPLLEILARELRRLGLRLRLFNIDMIR
SEQ ID NO:12               GSLSFSQVSNLPNEAHAGYYDDMR-LEDAIMPPTAPTKNLAAGLAR-LGLPLFKFDMIR
SEQ ID NO:14               DLMSFSQVSNLAVNDCDGYTRLMHLDDDTEMPPDAPVVDIAGGLRRALKLNLFNPDVIR
SEQ ID NO:16               GVPRFPRVSCAAASADDADLDPMT------AEHPPRPLLERLARELRHRLGLCLFNIDMIR
SEQ ID NO:18               GIYRFPRVSCAAASADDADLDPTV------AELPPRPLLEKILAKRLRWRLGJRLFNLDITR
SEQ ID NO:20               GSLPFSRVTSLGVEDEGGG------AVEDAEMPPQSLVGELARGLREALGLNLFNVDVIR
SEQ ID NO:22               -TERMSKTGCV------
SEQ ID NO:24               ------------------------------------------------------------
SEQ ID NO:26               ------EDSMPPAAFVDQVARGLRQALGLHLLNPDMFA
SEQ ID NO:28               ------------------------------------------------------------
SEQ ID NO:30               ------RRLGLRLFIISMIR
SEQ ID NO:32               CIFGLPGVCVAASSDHAALDPRI------AELPPRPLLEKLGRERRGRLGLRLFNIDMIR
```

Figure 1D

```
                          361                                                          420
SEQ ID NO:33 (gi 3396079) ----DAKDANRYLIIDINYFPGYAKMPSYEPVLTEFFWDMVT---------------------
SEQ ID NO:34 (gi 3660465) ----DAKDANRYLIIDINYFPGYAKMPSYEPVLTEFFWDMVT---------------------
SEQ ID NO:2               ----ELGTKDRYVIIDINVFPGYGKMPGYERMFTDFLLSLAQ---------------------
SEQ ID NO:4               ----EHGTRDHYYVIDINYFPGYGKMPEYEHIFTDFLLSLVQ---------------------
SEQ ID NO:6               ----DVRAGDRYLVTDINKTSCYAKMPGYETVY-GFL--------------------------
SEQ ID NO:8               ----EHGTRDRFYVIDMNYFPGYGKMPGYEHVFTDFLLSLVQ---------------------
SEQ ID NO:10              ----DPPAGNRYLVIDINYFPGYAKMPGYETVLTDFYWEMV----------------------
SEQ ID NO:12              ----DARYGNRYLIIDINYFPGYAKMPGYEAVLTQPPCEVML---------------------
SEQ ID NO:14              ----EYGTKDVFYVIDINYFPGYGKMPDYEHVFTDFLLSLVQ---------------------
SEQ ID NO:16              ----EYGTRNHFYVIDINYFPGYGKMPEYEHIFTDFLLSLGQ---------------------
SEQ ID NO:18              ----DGKEFTRYLVIDINYFPGYAKLPSYEPFITDFLLDIVR---------------------
SEQ ID NO:20              ATELDDGGRRRYFLVDINYFPGFAKMPGYETALIDFFAEMIQL--------------------
SEQ ID NO:22              ----EHGTRDRPYVIDMNYFPGYGKMPGYEHVFTDFLLSLDQ---------------------
SEQ ID NO:24              ----ELGANDRYIIDINYFPGYGKMPGYEHIFTDFLQSLGQ----------------------

421                                                          480
SEQ ID NO:33 (gi 3396079) ---------------------------------------------------
SEQ ID NO:34 (gi 3660465) ----KKNH---------------------------------------------
SEQ ID NO:2               ----KKNH---------------------------------------------
SEQ ID NO:4               ----SK-YK-----RYLS------GT.----
SEQ ID NO:6               ----------K
SEQ ID NO:8               ----SK.---------LGDGP.--------
SEQ ID NO:10              ----KEYK---RRPSYSS---CRG.----
SEQ ID NO:12              ----HKDDTPNLNPNPN--DEDVK
SEQ ID NO:14              ----KKKQQERQQQEEGNAPKBKEESLQ
SEQ ID NO:16              ----SN-CK------KKLA-----
SEQ ID NO:18              ----GK-YK------KK-------
SEQ ID NO:20              ----SKTA.------
SEQ ID NO:22              ----GTAGAAAGQEKLESVP---CNEL.
SEQ ID NO:24              ------DD----
SEQ ID NO:26              ----QKEYK---RRIGYTS----GEG.---
SEQ ID NO:28              ----NK-YQ------RCLS------GG.
```

Figure 1E

```
                            481              498
SEQ ID NO:33 (gi 3396079)   V----------------
SEQ ID NO:34 (gi 3660465)   V----------------
SEQ ID NO:2                 -----------------
SEQ ID NO:4                 L----------------
SEQ ID NO:6                 -----------------
SEQ ID NO:8                 -----------------
SEQ ID NO:10                -----------------
SEQ ID NO:12                -----------------
SEQ ID NO:14                .----------------
SEQ ID NO:16                -----------------
SEQ ID NO:18                A----------------
SEQ ID NO:20                T----------------
SEQ ID NO:22                -----------------
SEQ ID NO:24                -----------------
SEQ ID NO:26                -----------------
SEQ ID NO:28                -----------------
SEQ ID NO:30                G----------------
SEQ ID NO:32                -----------------
```

PHYTIC ACID BIOSYNTHETIC ENZYMES

This application is a divisional of U.S. application Ser. No. 10/324,316 filed Dec. 20, 2002, now granted as U.S. Pat. No. 6,855,869, which is a continuation of U.S. application Ser. No. 09/686,521, filed Oct. 11, 2000, now abandoned, which is a Continuation of Application of PCT/US99/08790, filed Apr. 22, 1999, which claims the benefit of U.S. Provisional Application No. 60/082,960, filed Apr. 24, 1998.

FIELD OF THE INVENTION

This invention is in the field of plant molecular biology. More specifically, this invention pertains to nucleic acid fragments encoding phytic acid biosynthetic enzymes in plants and seeds.

BACKGROUND OF THE INVENTION

Myo-inositol 1,2,3,4,5,6-hexaphosphate, commonly known as phytic acid, is an abundant molecule in many plant seeds and vegetative tissue such as roots and tubers (Hartland and Oberlaeas, (1986) *J. Assoc. Off. Anal. Chem.* 69:667–670). Phytic acid exists primarily as mixture of potassium, calcium, iron, zinc and magnesium phytate salts (Pernollet J. C. (1978) *Phytochemistry* 17:1473–1480).

In corn (*Zea mays* L.), 90% of the phytate is deposited in protein bodies localized in the germ whereas in legume crops 90% of the phytate is localized in the endosperm and cotyledons. Up to 80% of phytate is in the aluerone layer of wheat (*Triticum aestivum* Lam.) and rice (*Oryza sative* L.) (O'Dell B. L. et al. (1972) *J. Agric. Food Chem.* 20:718–721). The presence of phytate phosphorous in such food crops decreases the bioavailability of zinc by forming a very stable insoluble phytate zink complex, making the zinc unavailable in the intestinal mucosa of mammals (O'Dell, B. L., et al. (1972) *J. Agr. Food Chem.* 20:718–721). Although phytate phosphorous is readily available to ruminants, it is less available to monogastric animals. In addition to being only partially digestible, the presence of phytic acid in food crops leads to excretion of other limiting nutrients such as essential amino acids, calcium and zinc (Mroz, Z. et al. (1994) *J. Animal Sci.* 72:126–132; Fox et al., In Nutritional Toxicology Vol. 3, Academic Press, San Diego (1989) pp. 59–96).

Phytic acid is thought to arise in plants by two pathways. The first pathway uses free myo-inositol as the initial substrate, with subsequent phosphorylation by a phosphoinositol kinase. Contribution to the free myo-inositol pool is either by recycling from other pathways or by the dephosphorylation of myo-inositol-1-phosphate. The alternate pathway uses myo-inositol-1-phosphate as the initial substrate, with subsequent phosphorylations catalyzed by phosphoinositol kinase. The committed step for myo-inositol-1-phosphate production is the $NAD^+$-catalyzed oxidation of carbon 5 of the b-enantiomer of D-glucose-6-phosphate. This reaction is catalyzed by myo-inositol-1-phosphate synthase (Raboy, V. In Inositol Metabolism in Plants (1990) Wiley-Liss, New York, pp. 55–76).

Phytic acid is degraded in plant cells to D-myo-inositol 1,2,4,5,6-pentakisphosphate and orthophosphate through the action of phytase. Manipulation of this enzyme activity could lead to a reduction of phytic acid levels in seeds and an increase in inositol trisphosphate and free phosphate, thus making phosphorus more metabolically available to animals that are fed the seed. Another method to lower phytic acid levels is by inhibiting the activity of myo-inositol-1(or 4)-monophosphatase, which catalyzes the reaction: myo-inositol 1-phosphate+H2O=myo-inositol+orthophosphate. Manipulation of the activity of this enzyme in developing seeds could decrease phytic acid levels in seeds and increase levels of free phosphate. Lastly, phytic acid levels could also be reduced by inhibiting the activity of inositol trisphosphate kinase. This enzyme catalyzes the reaction: ATP+1D-myo-inositol 1,3,4-trisphosphate=ADP+1D-myo-inositol 1,3,4,6-tetrakisphosphate. This reaction is one of the final steps leading to the formation of Myo-Inositol 1,2,3,4,5,6-hexaphosphate (phytic acid). Reduction in the activity of the enzyme in developing seeds would interrupt phytic acid synthesis leaving the phosphate as the more metabolically available inositol trisphosphate and free phosphate.

In the United States, corn accounts for about 80% of the grain fed to all classes of livestock, including poultry, and is usually ground before feeding (Corn: Chemistry and Technology, 1987, American Association of Cereal Chemists, Inc., Edited by Stanley A. Watson and Paul E. Ramstad). A meal with decreased amounts of phytic acid and increased amounts of available phosphate would lead to improved feed efficiency in corn-containing rations, making available certain minerals especially zinc, magnesium, iron and calcium. Indeed, enzymatic treatment of soybean meal-containing rations to partially hydrolyze the phosphate groups from phytic acid improves both phosphate availability and the availability of other limiting nutrients. Also, in the wet milling of corn, phytate in the steepwater tends to precipitate, causing problems in handling, storing and transportation of the steep liquor. (Pen et al. (1993) *Biotechnology* 11:811–814). In light of these factors, it is apparent that corn plants with heritable, substantially reduced levels of phytic acid and increased levels of free phosphorous in their seeds would be desirable. Accordingly, the availability of nucleic acid sequences encoding all or a portion of these enzymes would facilitate studies to better understand carbohydrate metabolism and function in plants, provide genetic tools for the manipulation of these biosynthetic pathways, and provide a means to control carbohydrate transport and distribution in plant cells.

SUMMARY OF THE INVENTION

The instant invention relates to isolated nucleic acid fragments encoding phytic acid biosynthetic enzymes. Specifically, this invention concerns an isolated nucleic acid fragment encoding an inositol 1,3,4-triphosphate 5/6-kinase. In addition, this invention relates to a nucleic acid fragment that is complementary to the nucleic acid fragment encoding inositol 1,3,4-triphosphate 5/6-kinase. An additional embodiment of the instant invention pertains to a polypeptide encoding all or a substantial portion of an inositol 1,3,4-triphosphate 5/6-kinase.

In another embodiment, the instant invention relates to a chimeric gene encoding an inositol 1,3,4-triphosphate 5/6-kinase, or to a chimeric gene that comprises a nucleic acid fragment that is complementary to a nucleic acid fragment encoding an inositol 1,3,4-triphosphate 5/6-kinase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an inositol 1,3,4-triphosphate 5/6-kinase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an inositol 1,3,4-triphosphate 5/6-kinase in a transformed host cell comprising: a) transforming a host cell with a chimeric gene comprising a nucleic acid fragment encoding an inositol 1,3,4-triphosphate 5/6-kinase; and b) growing the transformed host cell under conditions that are suitable for expression of the chimeric gene wherein expression of the chimeric gene results in production of altered levels of inositol 1,3,4-triphosphate 5/6-kinase in the transformed host cell.

An addition embodiment of the instant invention concerns a method for obtaining a nucleic acid fragment encoding all or a substantial portion of an amino acid sequence encoding an inositol 1,3,4-triphosphate 5/6-kinase.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A, 1B, 1C, 1D and 1E show a comparison of the amino acid sequence set forth in SEQ ID NOs:2, 4, 6, 8, 10, 12, 14, 16, 18, 20, 22, 24, 26, 28, 30 and 32 with the *Arabidopsis thaliana* inositol 1,3,4-triphosphate 5/6-kinase amino acid sequences set forth in NCBI Identifier No. gi 3396079 (SEQ ID NO:33) and NCBI Identifier No. gi 3660465 (SEQ ID NO:34). Alignments were performed using the Clustal algorithm.

The following sequence descriptions and sequence listings attached hereto comply with the rules governing nucleotide and/or amino acid sequence disclosures in patent applications as set forth in 37 C.F.R. §1.821–1.825.

SEQ ID NO:1 is the nucleotide sequence comprising a contig assembled from the cDNA inserts in clones cca.pk0022.e6, cpe1c.pk001.h8, cr1n.pk0188.g8, p0005.cbmfp77r and p0090.cspsg46r encoding a corn inositol 1,3,4-triphosphate 5/6-kinase.

SEQ ID NO:2 is the deduced amino acid sequence of an inositol 1,3,4-triphosphate 5/6-kinase derived from the nucleotide sequence of SEQ ID NO:1.

SEQ ID NO:3 is the nucleotide sequence comprising a portion of the cDNA insert in clone dms2c.pk003.m14 encoding a portion of an african daisy inositol 1,3,4-triphosphate 5/6-kinase.

SEQ ID NO:4 is the deduced amino acid sequence of a portion of an inositol 1,3,4-triphosphate 5/6-kinase derived from the nucleotide sequence of SEQ ID NO:3.

SEQ ID NO:5 is the nucleotide sequence comprising a portion of the cDNA insert in clone ncs.pk0019.a6 encoding a portion of a Catalpa inositol 1,3,4-triphosphate 5/6-kinase.

SEQ ID NO:6 is the deduced amino acid sequence of a portion of an inositol 1,3,4-triphosphate 5/6-kinase derived from the nucleotide sequence of SEQ ID NO:5.

SEQ ID NO:7 is the nucleotide sequence comprising a contig assembled from the cDNA inserts in clones p0125.czaaj15r, p0125.czabg28r, p0125.czabp82r and p0041.crtcl17r encoding a corn inositol 1,3,4-triphosphate 5/6-kinase.

SEQ ID NO:8 is the deduced amino acid sequence of an inositol 1,3,4-triphosphate 5/6-kinase derived from the nucleotide sequence of SEQ ID NO:8.

SEQ ID NO:9 is the nucleotide sequence comprising a contig assembled from the cDNA inserts in clones rr1.pk0052.f1 and r10n.pk0015.b2 encoding a portion of a rice inositol 1,3,4-triphosphate 5/6-kinase.

SEQ ID NO:10 is the deduced amino acid sequence of a portion of an inositol 1,3,4-triphosphate 5/6-kinase derived from the nucleotide sequence of SEQ ID NO:9.

SEQ ID NO:11 is the nucleotide sequence comprising the entire cDNA insert in clone rlr12.pk0002.c11 encoding a rice inositol 1,3,4-triphosphate 5/6-kinase.

SEQ ID NO:12 is the deduced amino acid sequence of an inositol 1,3,4-triphosphate 5/6-kinase derived from the nucleotide sequence of SEQ ID NO:11.

SEQ ID NO:13 is the nucleotide sequence comprising a portion of the cDNA insert in clone rr1.pk0061.c5 encoding a portion of a rice inositol 1,3,4-triphosphate 5/6-kinase.

SEQ ID NO:14 is the deduced amino acid sequence of a portion of an inositol 1,3,4-triphosphate 5/6-kinase derived from the nucleotide sequence of SEQ ID NO:13.

SEQ ID NO:15 is the nucleotide sequence comprising the entire cDNA insert in clone sfl1.pk0091.c9 encoding a soybean inositol 1,3,4-triphosphate 5/6-kinase.

SEQ ID NO:16 is the deduced amino acid sequence of an inositol 1,3,4-triphosphate 5/6-kinase derived from the nucleotide sequence of SEQ ID NO:15.

SEQ ID NO:17 is the nucleotide sequence comprising the entire cDNA insert in clone sgs3n.pk001.b5 encoding a soybean inositol 1,3,4-triphosphate 5/6-kinase.

SEQ ID NO:18 is the deduced amino acid sequence of an inositol 1,3,4-triphosphate 5/6-kinase derived from the nucleotide sequence of SEQ ID NO:17.

SEQ ID NO:19 is the nucleotide sequence comprising a portion of the cDNA insert in clone s11.pk0026.a8 encoding a portion of a soybean inositol 1,3,4-triphosphate 5/6-kinase.

SEQ ID NO:20 is the deduced amino acid sequence of a portion of an inositol 1,3,4-triphosphate 5/6-kinase derived from the nucleotide sequence of SEQ ID NO:19.

SEQ ID NO:21 is the nucleotide sequence comprising a portion of the cDNA insert in clone sls2c.pk013.j24 encoding a portion of a soybean inositol 1,3,4-triphosphate 5/6-kinase.

SEQ ID NO:22 is the deduced amino acid sequence of a portion of an inositol 1,3,4-triphosphate 5/6-kinase derived from the nucleotide sequence of SEQ ID NO:21.

SEQ ID NO:23 is the nucleotide sequence comprising a portion of the cDNA insert in clone wdk4c.pk005.a15(5') encoding a portion of a wheat inositol 1,3,4-triphosphate 5/6-kinase.

SEQ ID NO:24 is the deduced amino acid sequence of a portion of an inositol 1,3,4-triphosphate 5/6-kinase derived from the nucleotide sequence of SEQ ID NO:23.

SEQ ID NO:25 is the nucleotide sequence comprising a portion of the cDNA insert in clone wdk4c.pk005.a15(3') encoding a portion of a wheat inositol 1,3,4-triphosphate 5/6-kinase.

SEQ ID NO:26 is the deduced amino acid sequence of a portion of an inositol 1,3,4-triphosphate 5/6-kinase derived from the nucleotide sequence of SEQ ID NO:25.

SEQ ID NO:27 is the nucleotide sequence comprising a portion of the cDNA insert in clone wr1.pk0137.c5(5') encoding a portion of a wheat inositol 1,3,4-triphosphate 5/6-kinase.

SEQ ID NO:28 is the deduced amino acid sequence of a portion of an inositol 1,3,4-triphosphate 5/6-kinase derived from the nucleotide sequence of SEQ ID NO:27.

SEQ ID NO:29 is the nucleotide sequence comprising a portion of the cDNA insert in clone wr1.pk0137.c5(3') encoding a portion of a wheat inositol 1,3,4-triphosphate 5/6-kinase.

SEQ ID NO:30 is the deduced amino acid sequence of a portion of an inositol 1,3,4-triphosphate 5/6-kinase derived from the nucleotide sequence of SEQ ID NO:30.

SEQ ID NO:31 is the nucleotide sequence comprising a portion of the cDNA insert in clone wr1.pk0150.e10 encoding a portion of a wheat inositol 1,3,4-triphosphate 5/6-kinase.

SEQ ID NO:32 is the deduced amino acid sequence of a portion of an inositol 1,3,4-triphosphate 5/6-kinase derived from the nucleotide sequence of SEQ ID NO:31.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence.

"Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent similarity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% similar to the amino acid sequences reported herein. More preferred nucleic acid fragments encode amino acid sequences that are 90% similar to the amino acid sequences reported herein. Most preferred are nucleic acid fragments that encode amino acid sequences that are 95% similar to the amino acid sequences reported herein. Sequence alignments and percent similarity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABIOS.* 5:151–153) with the default parameters (GAP PENALTY=10, GAP LENGTH PENALTY=10) (hereafter, Clustal algorithm). Default parameters for pair-wise alignments using the Clustal method were KTUPLE 1, GAP PENALTY=3, WINDOW=5 and DIAGONALS SAVED=5.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410. In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the inositol 1,3,4-triphosphate 5/6-kinase proteins as set forth in SEQ ID NOs:2, 4, 6, 8, 10, 12, 14, 16, 18, 20, 22, 24, 26, 28, 30 and 32. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) Meth. Enzymol. 143:277) and particle-accelerated or "gene gun" transformation technology (Klein et al. (1987) Nature (London) 327:70–73; U.S. Pat. No. 4,945,050).

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Maniatis").

Nucleic acid fragments encoding at least a portion of several phytic acid biosynthetic enzymes have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Phytic Acid Biosynthetic Enzymes

| Enzyme | Clone | Plant |
|---|---|---|
| Inositol 1,3,4-trisphosphate 5/6-kinase | cca.pk0022.e6 | Corn |
| | cpe1c.pk001.h8 | Corn |
| | cr1n.pk0188.g8 | Corn |
| | dms2c.pk003.m14 | African daisy |
| | ncs.pk0019.a6 | Catalpa |
| | p0005.cbmfp77r | Corn |
| | p0041.crtcl17r | Corn |
| | p0090.cspsg46r | Corn |
| | p0125.czaaj15r | Corn |
| | p0125.czabg28r | Corn |
| | p0125.czabp82r | Corn |
| | r10n.pk0015.b2 | Rice |
| | rlr12.pk0012.c11 | Rice |
| | rr1.pk0052.f1 | Rice |
| | rr1.pk0061.c5 | Rice |
| | sfl1.pk0091.c9 | Soybean |
| | sgs3n.pk001.b5 | Soybean |
| | sl1.pk0026.a8 | Soybean |
| | sls2c.pk013.j24 | Soybean |
| | wdk4c.pk005.a15(5') | Wheat |
| | wdk4c.pk005.a15(3') | Wheat |
| | wr1.pk0137.c5(5') | Wheat |
| | wr1.pk0137.c5(3') | Wheat |
| | wr1.pk0150.e10 | Wheat |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other inositol 1,3,4-triphosphate 5/6-kinases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed inositol 1,3,4-triphosphate 5/6-kinases are present at higher or lower levels than normal or in cell types or developmental stages in which they are not normally found. This would have the effect of altering the level of inositol 1,3,4-triphosphate 5/6-kinase in those cells.

Overexpression of the inositol 1,3,4-triphosphate 5/6-kinase proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant phytic acid biosynthetic enzymes to different cellular compartments, or to facilitate its secretion from the cell. It is thus envisioned that the chimeric gene described above may be further supplemented by altering the coding sequence to encode an inositol 1,3,4-triphosphate 5/6-kinase with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding inositol 1,3,4-triphosphate 5/6-kinase in plants for some applications. In order to accomplish this, a chimeric gene designed for co-suppression of the instant phytic acid biosynthetic enzymes can be constructed by linking a gene or gene fragment encoding an inositol 1,3,4-triphosphate 5/6-kinase to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant inositol 1,3,4-triphosphate 5/6-kinases (or portions thereof) may be produced in heterologous host cells, particularly in the cells of microbial hosts, and can be used to prepare antibodies to the these proteins by methods well known to those skilled in the art. The antibodies are useful for detecting inositol 1,3,4-triphosphate 5/6-kinase in situ in cells or in vitro in cell extracts. Preferred heterologous host cells for production of the instant inositol 1,3,4-triphosphate 5/6-kinases are microbial hosts. Microbial expression systems and expression vectors containing regulatory sequences that direct high level expression of foreign proteins are well known to those skilled in the art. Any of these could be used to construct a chimeric gene for production of the instant inositol 1,3,4-triphosphate 5/6-kinases. This chimeric gene could then be introduced into appropriate microorganisms via transformation to provide high level expression of the encoded phytic acid biosynthetic enzyme. An example of a vector for high level expression of the instant inositol 1,3,4-triphosphate 5/6-kinases in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1): 37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the inositol 1,3,4-triphosphate 5/6-kinase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding an inositol 1,3,4triphosphate 5/6-kinase can be identified and obtained. This mutant plant can then be used to determine or confirm the natural function of the inositol 1,3,4-triphosphate 5/6-kinase gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various african daisy, Catalpa, corn, rice, soybean and wheat tissues were prepared. The characteristics of the libraries are described below.

TABLE 2 cDNA Libraries from African Daisy, *Catalpa*, Corn, Rice, Soybean and Wheat

| Library | Tissue | Clone |
|---|---|---|
| cca | Corn (*Zea mays* L.) type II callus tissue, undifferentiated, highly transformable | cca.pk0022.e6 |
| cpe1c | Corn (*Zea mays* L.) pooled BMS treated with chemicals related to phosphatase*** | cpe1c.pk001.h8 |
| cr1n | Corn (*Zea mays* L.) root from 7 day seedlings grown in light* | cr1n.pk0188.g8 |
| dms2c | African daisy (*Dimorphotheca sinuata*) developing seeds | dms2c.pk003.m14 |
| ncs | *Catalpa speciosa* developing seed | ncs.pk0019.a6 |
| p0005 | Corn (*Zea mays* L.) immature ear | p0005.cbmfp77r |
| p0041 | Corn (*Zea mays* L.) root tips (four days after imbibition), smaller than 5 mm in length. | p0041.crtcl17r |
| p0090 | Corn (*Zea mays* L.) heat shocked seedling after 10 day drought stress (heat shocked for 8, 16, 24 hours at 45 C.) pooled for library construction* | p0090.cspsg46r |
| p0125 | Corn (*Zea mays* L.) anther: prophase I | p0125.czaaj15r<br>p0125.czabg28r<br>p0125.czabp82r |
| rl0n | Rice (*Oryza sativa* L.) 15 day leaf* | rl0n.pk0015.b2 |
| rlr12 | Rice (*Oryza sativa* L.) leaf, 15 days after germination, 12 hours after infection of *Magaporthe grisea* strain 4360-R-62 (AVR2-YAMO) | rlr12.pk0012.c11 |
| rr1 | Rice (*Oryza sativa* L.) root of two week old developing seedling | rr1.pk0052.f1<br>rr1.pk0061.c5 |
| sfl1 | Soybean (*Glycine max* L.) immature flower | sfl1.pk0091.c9 |
| sgs3n | Soybean (*Glycine max* L.) seeds 25 hrs after germination | sgs3n.pk001.b5 |
| sl1 | Soybean (*Glycine max* L.) two week old developing seedlings treated with water | sl1.pk0026.a8 |
| sls2c | Soybean (*Glycine max* L.) infected with *Sclerotinia sclerotiorum* mycelium | sls2c.pk013.j24 |
| wdk4c | Wheat (*Triticum aestivum* L.) developing kernel, 21 days after anthesis | wdk4c.pk005.a15(5')<br>wdk4c.pk005.a15(3') |
| wr1 | Wheat (*Triticum aestivum* L.) root; 7 day old seedling, light grown | wr1.pk0137.c5(5')<br>wr1.pk0137.c5(3')<br>wr1.pk0150.e10 |

*These libraries were normalized essentially as described in U.S. Pat. No. 5,482,845
**V-12 refers to stages of corn growth. The descriptions can be found in "How a Corn Plant Develops" Special Report No. 48, Iowa State University of Science and Technology Cooperative Extension Service Ames, Iowa, Reprinted February 1996.
***Chemicals related to phosphatase: okadaic acid, cyclosporin A, calyculin A and cypermethrin Sigma Chemical Co. and Calbiochem-Novabiochem Corp Calbiochem.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding phytic acid biosynthetic enzymes were identified by conducting BLAST (Basic Local Alignment Search Tool; Altschul, S. F., et al., (1993) *J. Mol. Biol.* 215:403–410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272 and Altschul, Stephen F., et al. (1997) *Nucleic Acids Res.* 25:3389–3402) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Inositol 1,3,4-Triphosphate 5/6-Kinase The BLASTX search using the EST sequences from clones cca.pk0022.e6, cpe1c.pk001.h8, cr1n.pk0188.g8, dms2c.pk003.m14, rlr12.pk0012.c11, rr1.pk006.c5, sfl1.pk0091.c9, sls2c.pk013.j24, wdk4c.pk005.a15(5'), wdk4c.pk005.a15(3'), wr1.pk0137.c5(5'), wr1.pk0137.c5 (3') and wr1.pk0150.e10 revealed similarity of the proteins encoded by the cDNAs to inositol 1,3,4-triphosphate 5/6-kinase from *Arabidopsis thaliana* (NCBI Identifier No. gi 3396079).

The BLASTX search using the EST sequences from clones ncs.pk0019.a6, p0125.czaaj15r, p0125.czabg28r, p0125.czabp82r, p0041.crtcl17r, rr1.pk0052.f1, r10n.pk0015.b2, sgs3n.pk001.b5 and s11.pk0026.a8 revealed similarity of the proteins encoded by the cDNAs to inositol 1,3,4-triphosphate 5/6-kinase from *Arabidopsis thaliana* (NCBI Identifier No. gi 3660465).

In the process of comparing the ESTs it was found that several had overlapping regions of homology. Using this homology it was possible to align the ESTs and assemble several contigs encoding unique inositol 1,3,4-triphosphate 5/6-kinase proteins. The composition of each of the assembled contigs is shown in Table 3.

The BLAST results for each of the ESTs and the contigs are also shown in Table 3:

TABLE 3

BLAST Results for Clones Encoding Polypeptides Homologous to *Arabidopsis thaliana* Inositol 1,3,4-Triphosphate 5/6-Kinase

| Clone | BLAST pLog Score |
|---|---|
| Contig composed of clones: | 67.40 |
| cca.pk0022.e6 | |
| cpe1c.pk001.h8 | |
| cr1n.pk0188.g8 | |
| p0005.cbmfb77r | |
| p0090.cspsg46r | |
| dms2c.pk003.m14 | 25.15 |
| ncs.pk0019.a6 | 48.52 |
| Contig composed of clones: | 74.05 |
| p0125.czaaj15r | |
| p0125.czabg28r | |
| p0125.czabp82r | |
| p0041.crtcl17r | |
| Contig composed of | 44.15 |
| rr1.pk0052.f1 | |
| r10n.pk0015.b2 | |
| rlr12.pk0012.c11 | 96.22 |
| rr1.pk0061.c5 | 21.30 |
| sfl1.pk0091.c9 | 107.00 |
| sgs3n.pk001.b5 | 72.52 |
| sl1.pk0026.a8 | 24.70 |
| sls2c.pk013.j24 | 102.00 |
| wdk4c.pk005.a15(5') | 21.10 |
| wdk4c.pk005.a15(3') | 15.52 |
| wr1.pk0137.c5(5') | 29.00 |
| wr1.pk0137.c5(3') | 6.70 |
| wr1.pk0150.e10 | 59.00 |

The sequence of the corn contig composed of clones cca.pk0022.e6, cpe1c.pk001.h8, cr1n.pk0188.g8, p0005.cbmfp77r and p0090.cspsg46r is shown in SEQ ID NO:1; the deduced amino acid sequence of this cDNA, which represents 100% of the of the protein, is shown in SEQ ID NO:2. The amino acid sequence set forth in SEQ ID NO:2 was evaluated by BLASTP, yielding a pLog value of 59.22 versus the *Arabidopsis thaliana* sequence. A calculation of the percent similarity of the amino acid sequence set forth in SEQ ID NO:2 and the *Arabidopsis thaliana* sequence (using the Clustal algorithm) revealed that the protein encoded by SEQ ID NO:2 is 37% similar to the *Arabidopsis thaliana* inositol 1,3,4-triphosphate 5/6-kinase.

The sequence of a portion of the cDNA insert from clone dms2c.pk003.m14 is shown in SEQ ID NO:3; the deduced amino acid sequence of this cDNA, which represents 35% of the of the protein (N-terminal region), is shown in SEQ ID NO:4. A calculation of the percent similarity of the amino acid sequence set forth in SEQ ID NO:4 and the *Arabidopsis thaliana* sequence (using the Clustal algorithm) revealed that the protein encoded by SEQ ID NO:4 is 37% similar to the *Arabidopsis thaliana* inositol 1,3,4-triphosphate 5/6-kinase.

The sequence of a portion of the cDNA insert from clone ncs.pk0019.a6 is shown in SEQ ID NO:5; the deduced amino acid sequence of this cDNA, which represents 73% of the of the protein (C-terminal region), is shown in SEQ ID NO:6. The amino acid sequence set forth in SEQ ID NO:6 was evaluated by BLASTP, yielding a pLog value of 46.52 versus the *Arabidopsis thaliana* sequence. A calculation of the percent similarity of the amino acid sequence set forth in SEQ ID NO:6 and the *Arabidopsis thaliana* sequence (using the Clustal algorithm) revealed that the protein encoded by SEQ ID NO:6 is 39% similar to the *Arabidopsis thaliana* inositol 1,3,4-triphosphate 5/6-kinase.

The sequence of the corn contig composed of clones p0125.czaaj15r, p0125.czabg28r, p0125.czabp82r and p0041.crtcl17r is shown in SEQ ID NO:7; the deduced amino acid sequence of this cDNA, which represents 100% of the of the protein, is shown in SEQ ID NO:8. The amino acid sequence set forth in SEQ ID NO:8 was evaluated by BLASTP, yielding a pLog value of 84.40 versus the *Arabidopsis thaliana* sequence. A calculation of the percent similarity of the amino acid sequence set forth in SEQ ID NO:8 and the *Arabidopsis thaliana* sequence (using the Clustal algorithm) revealed that the protein encoded by SEQ ID NO:8 is 48% similar to the *Arabidopsis thaliana* inositol 1,3,4-triphosphate 5/6-kinase.

The sequence of the rice contig composed of clones rr1.pk0052.f1 and r10n.pk0015.b2 is shown in SEQ ID NO:9; the deduced amino acid sequence of this cDNA, which represents 77% of the of the protein (C-terminal region), is shown in SEQ ID NO:10. The amino acid sequence set forth in SEQ ID NO:10 was evaluated by BLASTP, yielding a pLog value of 43.70 versus the *Arabidopsis thaliana* sequence. A calculation of the percent similarity of the amino acid sequence set forth in SEQ ID NO:10 and the *Arabidopsis thaliana* sequence (using the Clustal algorithm) revealed that the protein encoded by SEQ ID NO:10 is 37% similar to the *Arabidopsis thaliana* inositol 1,3,4-triphosphate 5/6-kinase.

The sequence of the entire cDNA insert from clone rlr12.pk0012.c11 is shown in SEQ ID NO:11; the deduced amino acid sequence of this cDNA, which represents 100% of the of the protein, is shown in SEQ ID NO:12. The amino acid sequence set forth in SEQ ID NO:12 was evaluated by BLASTP, yielding a pLog value of 96.40 versus the *Arabidopsis thaliana* sequence. A calculation of the percent similarity of the amino acid sequence set forth in SEQ ID NO:12 and the *Arabidopsis thaliana* sequence (using the Clustal algorithm) revealed that the protein encoded by SEQ ID NO:12 is 53% similar to the *Arabidopsis thaliana* inositol 1,3,4-triphosphate 5/6-kinase.

The sequence of a portion of the cDNA insert from clone rr1.pk0061.c5 is shown in SEQ ID NO:13; the deduced amino acid sequence of this cDNA, which represents 41% of the of the protein (N-terminal region), is shown in SEQ ID NO:14. A calculation of the percent similarity of the amino acid sequence set forth in SEQ ID NO:14 and the *Arabidopsis thaliana* sequence (using the Clustal algorithm) revealed that the protein encoded by SEQ ID NO:14 is 36% similar to the *Arabidopsis thaliana* inositol 1,3,4-triphosphate 5/6-kinase.

The sequence of the entire cDNA insert from clone sfl1.pk0091.c9 is shown in SEQ ID NO:15; the deduced amino acid sequence of this cDNA, which represents 100% of the of the protein, is shown in SEQ ID NO:16. The amino acid sequence set forth in SEQ ID NO:16 was evaluated by BLASTP, yielding a pLog value of 94.70 versus the *Arabidopsis thaliana* sequence. A calculation of the percent similarity of the amino acid sequence set forth in SEQ ID NO:16 and the *Arabidopsis thaliana* sequence (using the Clustal algorithm) revealed that the protein encoded by SEQ ID NO:16 is 53% similar to the *Arabidopsis thaliana* inositol 1,3,4-triphosphate 5/6-kinase.

The sequence of the entire cDNA insert from clone sgs3n.pk001.b5 is shown in SEQ ID NO:17; the deduced amino acid sequence of this cDNA, which represents 100% of the of the protein, is shown in SEQ ID NO:18. The amino acid sequence set forth in SEQ ID NO:18 was evaluated by BLASTP, yielding a pLog value of 67.00 versus the *Arabidopsis thaliana* sequence. A calculation of the percent similarity of the amino acid sequence set forth in SEQ ID NO:18 and the *Arabidopsis thaliana* sequence (using the Clustal algorithm) revealed that the protein encoded by SEQ ID NO:18 is 40% similar to the *Arabidopsis thaliana* inositol 1,3,4-triphosphate 5/6-kinase.

The sequence of a portion of the cDNA insert from clone sl1.pk0026.a8 is shown in SEQ ID NO:19; the deduced amino acid sequence of this cDNA, which represents 41% of the of the protein (C-terminal region), is shown in SEQ ID NO:20. The amino acid sequence set forth in SEQ ID NO:20 was evaluated by BLASTP, yielding a pLog value of 22.70 versus the *Arabidopsis thaliana* sequence. A calculation of the percent similarity of the amino acid sequence set forth in SEQ ID NO:20 and the *Arabidopsis thaliana* sequence (using the Clustal algorithm) revealed that the protein encoded by SEQ ID NO:20 is 40% similar to the *Arabidopsis thaliana* inositol 1,3,4-triphosphate 5/6-kinase.

The sequence of the entire cDNA insert from clone sls2c.pk013.j24 is shown in SEQ ID NO:21; the deduced amino acid sequence of this cDNA, which represents 99% of the of the protein, is shown in SEQ ID NO:22. The amino acid sequence set forth in SEQ ID NO:22 was evaluated by BLASTP, yielding a pLog value of 92.00 versus the *Arabidopsis thaliana* sequence. A calculation of the percent similarity of the amino acid sequence set forth in SEQ ID NO:22 and the *Arabidopsis thaliana* sequence (using the Clustal algorithm) revealed that the protein encoded by SEQ ID NO:22 is 51% similar to the *Arabidopsis thaliana* inositol 1,3,4-triphosphate 5/6-kinase.

The sequence of a portion of the cDNA insert from clone wdk4c.pk005.a15(5') is shown in SEQ ID NO:23; the deduced amino acid sequence of this cDNA, which represents 51% of the of the protein (N-terminal region), is shown in SEQ ID NO:24. A calculation of the percent similarity of the amino acid sequence set forth in SEQ ID NO:24 and the *Arabidopsis thaliana* sequence (using the Clustal algorithm) revealed that the protein encoded by SEQ ID NO:24 is 32% similar to the *Arabidopsis thaliana* inositol 1,3,4-triphosphate 5/6-kinase.

The sequence of a portion of the cDNA insert from clone wdk4c.pk005.a15(3') is shown in SEQ ID NO:25; the deduced amino acid sequence of this cDNA, which represents 31% of the of the protein (C-terminal region), is shown in SEQ ID NO:26. A calculation of the percent similarity of the amino acid sequence set forth in SEQ ID NO:26 and the *Arabidopsis thaliana* sequence (using the Clustal algorithm) revealed that the protein encoded by SEQ ID NO:26 is 29% similar to the *Arabidopsis thaliana* inositol 1,3,4-triphosphate 5/6-kinase.

The sequence of a portion of the cDNA insert from clone wr1.pk0137.c5(5') is shown in SEQ ID NO:27; the deduced amino acid sequence of this cDNA, which represents 50% of the of the protein (middle region), is shown in SEQ ID NO:28. A calculation of the percent similarity of the amino acid sequence set forth in SEQ ID NO:28 and the *Arabidopsis thaliana* sequence (using the Clustal algorithm) revealed that the protein encoded by SEQ ID NO:28 is 40% similar to the *Arabidopsis thaliana* inositol 1,3,4-triphosphate 5/6-kinase.

The sequence of a portion of the cDNA insert from clone wr1.pk0137.c5(3') is shown in SEQ ID NO:29; the deduced amino acid sequence of this cDNA, which represents 21% of the of the protein (C-terminal region), is shown in SEQ ID NO:30. A calculation of the percent similarity of the amino acid sequence set forth in SEQ ID NO:30 and the *Arabidopsis thaliana* sequence (using the Clustal algorithm) revealed that the protein encoded by SEQ ID NO:30 is 35% similar to the *Arabidopsis thaliana* inositol 1,3,4-triphosphate 5/6-kinase.

The sequence of a portion of the cDNA insert from clone wr1.pk0150.e10 is shown in SEQ ID NO:31; the deduced amino acid sequence of this cDNA, which represents 88% of the of the protein (C-terminal region), is shown in SEQ ID NO:32. The amino acid sequence set forth in SEQ ID NO:32 was evaluated by BLASTP, yielding a pLog value of 51.15 versus the *Arabidopsis thaliana* sequence. A calculation of the percent similarity of the amino acid sequence set forth in SEQ ID NO:32 and the *Arabidopsis thaliana* sequence (using the Clustal algorithm) revealed that the protein encoded by SEQ ID NO:32 is 38% similar to the *Arabidopsis thaliana* inositol 1,3,4-triphosphate 5/6-kinase.

FIGS. 1A, 1B, 1C, 1D and 1E presents an alignment of the amino acid sequence set forth in SEQ ID NOs:2, 4, 6, 8, 10, 12, 14, 16, 18, 20, 22, 24, 26, 28, 30 and 32 with the *Arabidopsis thaliana* inositol 1,3,4-triphosphate 5/6-kinase amino acid sequences, SEQ ID NO:33 (NCBI Identifier No. gi 3396079) and SEQ ID NO:34 (NCBI Identifier No. gi 3660465). Alignments were performed using the Clustal algorithm.

These sequences represent the first african daisey, Catalpa, corn, rice, soybean and wheat sequences encoding inositol 1,3,4-triphosphate 5/6-kinase proteins.

Example 4

Expression of Chimeric Genes in Monocot Cells

A chimeric gene comprising a cDNA encoding phytic acid biosynthetic enzyme in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL 1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a phytic acid biosynthetic enzymes, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 µm in diameter) are coated with DNA using the following technique. Ten µg of plasmid DNAs are added to 50 µL of a suspension of gold particles (60 mg per mL). Calcium chloride (50 µL of a 2.5 M solution) and spermidine free base (20 µL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 µL of absolute ethanol, centrifuged again and the supernatant removed. The ethanol rinse is performed again and the particles resuspended in a final volume of 30 µL of ethanol. An aliquot (5 µL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant phytic acid biosynthetic enzymes in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising a sequence encoding a phytic acid biosynthetic enzyme. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) Nature (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the $^{35}$S promoter from Cauliflower Mosaic Virus (Odell et al. (1985) Nature 313:810–812), the hygromycin phosphotransferase gene from plasmid pJR225 (from E. coli; Gritz et al. (1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the phytic acid biosynthetic enzyme and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant phytic acid biosynthetic enzymes can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as decribed above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the phytic acid biosynthetic enzyme are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-α-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
    (a) a nucleotide sequence encoding a polypeptide having inositol 1,3,4-triphosphate 5/6-kinase activity, wherein the polypeptide has an amino acid sequence of at least 90% sequence identity, based on the Clustal method of alignment, when compared to SEQ ID NO:8, or
    (b) a full-length complement of the nucleotide sequence of (a).

2. The polynucleotide of claim 1, wherein the amino acid sequence of the polypeptide has at least 95% sequence identity, based on the Clustal method of alignment, when compared to SEQ ID NO:8.

3. The polynucleotide of claim 1, wherein the amino acid sequence of the polypeptide comprises SEQ ID NO:8.

4. The polynucleotide of claim 1, wherein the nucleotide sequence comprises SEQ ID NO:7.

5. A vector comprising the polynucleotide of claim 1.

6. A recombinant DNA construct comprising the polynucleotide of claim 1 operably linked to suitable regulatory sequences.

7. A method for transforming a cell, comprising transforming a cell with the polynucleotide of claim 1.

8. A cell comprising the recombinant DNA construct of claim 6.

9. A plant comprising the recombinant DNA construct of claim 6.

10. A seed comprising the recombinant DNA construct of claim 6.

* * * * *

UNITED STATES PATENT AND TRADEMARK OFFICE
CERTIFICATE OF CORRECTION

PATENT NO. : 7,271,317 B2 Page 1 of 1
APPLICATION NO. : 11/038329
DATED : September 18, 2007
INVENTOR(S) : Rebecca E. Cahoon and William D. Hitz It is certified that error appears in the above-identified patent and that said Letters Patent is hereby corrected as shown below:

Title Page
Item [75], Inventors, delete "Richard W. Pearlstein" and "Thomas J. Carlson".

Signed and Sealed this

Thirteenth Day of May, 2008

JON W. DUDAS
*Director of the United States Patent and Trademark Office*

SEQUENCE LISTING

<160> NUMBER OF SEQ ID NOS: 34

<210> SEQ ID NO 1
<211> LENGTH: 1589
<212> TYPE: DNA
<213> ORGANISM: Zea mays
<220> FEATURE:
<221> NAME/KEY: unsure
<222> LOCATION: (410)
<220> FEATURE:
<221> NAME/KEY: unsure
<222> LOCATION: (478)
<220> FEATURE:
<221> NAME/KEY: unsure
<222> LOCATION: (492)
<220> FEATURE:
<221> NAME/KEY: unsure
<222> LOCATION: (519)
<220> FEATURE:
<221> NAME/KEY: unsure
<222> LOCATION: (525)..(526)
<220> FEATURE:
<221> NAME/KEY: unsure
<222> LOCATION: (534)
<220> FEATURE:
<221> NAME/KEY: unsure
<222> LOCATION: (557)

<400> SEQUENCE: 1

```
ttattaacag ctccgcggtc cctccctccc tcggtcggtc ggcgtcggtc cctctccctc      60
cccacccagt tagtcctcag cctatcccgt gcccgcgcag agcaccgcct ctgctcgacc     120
caccaccctc tgtgcagagt taattaacct tgaggtttcc gattgcccct cccttccgtt     180
cctctcgccc attcgcggcg agattcagcg gcaaggatgc gcctgcacgc ggaggtgcgg     240
gatgagatgg aggaggggag cgaggtgggg gctgtgacgg cttcggcggg gctgtcgcca     300
ccgccactca tcggtgcggc ggcgccggtt ccccggatag tggtggggtt cgccctcacg     360
aagaagaagg tgaagagctt cctgcagccc aagctgctcc tgctggccan gaagaatgga     420
atcagttttg tatctattga tgagtctctt cccctctcag aacaaggccc ttttgatntt     480
attttacaca anattactag gaaggagtgg cagaaggtnc tggannacta tcangaagaa     540
catccagaag ttactgncct tgacccacca aatgctatcg agcatctgaa caatcgacaa     600
tcaatgcttg aagaagtagc tgatttgaac ctgtcaaatt tctatggaga gtttgtatc      660 ccacgccagc tggtcattac gaaagatcca tcctctatac caacttctgt agctatggct     720
ggactaactt tgcccttggt tgccaagcca ttggttgttg atgggacgtc taaaggtcat     780
gaactatatc ttgcatatga cgaggcatcc ttgtcaatgc ttgatccgcc tctggttcta     840
caggaattca taaaccatgg cgggatcctc tttaaggtgt atatcattgg tgaaacaata     900
caggttgtcc gcaggttctc tcttcctgat gttaacacat atgacttact aaacaacgtt     960
ggcatctatc gattgccaag agtttcatgt gctgcagcta gtgcggatga tgcagatctt    1020
gaccctctta ttgcagagct tcctccaagg ccacttctag agaaactggg cagggagctt    1080
cgtggccgct ttggtttgag attgttcaat atagatatga ttagagaact tggaaccaaa    1140
gatcggtact acataattga tatcaactac ttcccaggtt acggcaaaat gccaggatat    1200
gagcgcatgt tcacagactt cttactaagt ctcgcacaaa gcaagtacaa aaggtactta    1260
agcgggacgt gaggtgcaag gaagtttgtg aagaccatgc tactgacgag atggcatata    1320
acggtggcag ctatgcttcc ccaccgcgcc aatgtacatt tgctggagac ataagcataa    1380
```

```
gccggaggct tgaggaagtt ggcaagtctc agtgtgtgtg ttcaaaatcg gtggcacatg   1440
ctggactgga gtaggaaata accaaggaaa cgcttggatg cgctgtaccc atgttgtaaa   1500
atgtttaact gaatgaacac cttcctcgtg atggctccct ccatcgtaat ttggcaacca   1560
tgagaattaa ttctgcaaaa aaaaaaaaa                                    1589
```

<210> SEQ ID NO 2
<211> LENGTH: 351
<212> TYPE: PRT
<213> ORGANISM: Zea mays
<220> FEATURE:
<221> NAME/KEY: UNSURE
<222> LOCATION: (65)
<220> FEATURE:
<221> NAME/KEY: UNSURE
<222> LOCATION: (88)
<220> FEATURE:
<221> NAME/KEY: UNSURE
<222> LOCATION: (92)
<220> FEATURE:
<221> NAME/KEY: UNSURE
<222> LOCATION: (103)..(104)
<220> FEATURE:
<221> NAME/KEY: UNSURE
<222> LOCATION: (106)
<220> FEATURE:
<221> NAME/KEY: UNSURE
<222> LOCATION: (114)

<400> SEQUENCE: 2

```
Met Arg Leu His Ala Glu Val Arg Asp Glu Met Glu Glu Gly Ser Glu
 1               5                  10                  15

Val Gly Ala Val Thr Ala Ser Ala Gly Leu Ser Pro Pro Leu Ile
             20                  25                  30

Gly Ala Ala Pro Val Pro Arg Ile Val Val Gly Phe Ala Leu Thr
         35                  40                  45

Lys Lys Lys Val Lys Ser Phe Leu Gln Pro Lys Leu Leu Leu Ala
     50                  55                  60

Xaa Lys Asn Gly Ile Ser Phe Val Ser Ile Asp Glu Ser Leu Pro Leu
 65                  70                  75                  80

Ser Glu Gln Gly Pro Phe Asp Xaa Ile Leu His Xaa Ile Thr Arg Lys
                 85                  90                  95

Glu Trp Gln Lys Val Leu Xaa Xaa Tyr Xaa Glu Glu His Pro Glu Val
                100                 105                 110

Thr Xaa Leu Asp Pro Pro Asn Ala Ile Glu His Leu Asn Asn Arg Gln
            115                 120                 125

Ser Met Leu Glu Glu Val Ala Asp Leu Asn Leu Ser Asn Phe Tyr Gly
        130                 135                 140

Glu Val Cys Ile Pro Arg Gln Leu Val Ile Thr Lys Asp Pro Ser Ser
145                 150                 155                 160

Ile Pro Thr Ser Val Ala Met Ala Gly Leu Thr Leu Pro Leu Val Ala
                165                 170                 175

Lys Pro Leu Val Val Asp Gly Thr Ser Lys Gly His Glu Leu Tyr Leu
            180                 185                 190

Ala Tyr Asp Glu Ala Ser Leu Ser Met Leu Asp Pro Pro Leu Val Leu
        195                 200                 205

Gln Glu Phe Ile Asn His Gly Gly Ile Leu Phe Lys Val Tyr Ile Ile
    210                 215                 220

Gly Glu Thr Ile Gln Val Val Arg Arg Phe Ser Leu Pro Asp Val Asn
225                 230                 235                 240
```

```
Thr Tyr Asp Leu Leu Asn Asn Val Gly Ile Tyr Arg Leu Pro Arg Val
                245                 250                 255

Ser Cys Ala Ala Ala Ser Ala Asp Asp Ala Asp Leu Asp Pro Leu Ile
            260                 265                 270

Ala Glu Leu Pro Pro Arg Pro Leu Leu Glu Lys Leu Gly Arg Glu Leu
        275                 280                 285

Arg Gly Arg Phe Gly Leu Arg Leu Phe Asn Ile Asp Met Ile Arg Glu
    290                 295                 300

Leu Gly Thr Lys Asp Arg Tyr Tyr Ile Ile Asp Ile Asn Tyr Phe Pro
305                 310                 315                 320

Gly Tyr Gly Lys Met Pro Gly Tyr Glu Arg Met Phe Thr Asp Phe Leu
                325                 330                 335

Leu Ser Leu Ala Gln Ser Lys Tyr Lys Arg Tyr Leu Ser Gly Thr
            340                 345                 350
```

<210> SEQ ID NO 3
<211> LENGTH: 494
<212> TYPE: DNA
<213> ORGANISM: Dimorphotheca sinuata
<220> FEATURE:
<221> NAME/KEY: unsure
<222> LOCATION: (7)
<220> FEATURE:
<221> NAME/KEY: unsure
<222> LOCATION: (179)
<220> FEATURE:
<221> NAME/KEY: unsure
<222> LOCATION: (392)
<220> FEATURE:
<221> NAME/KEY: unsure
<222> LOCATION: (405)
<220> FEATURE:
<221> NAME/KEY: unsure
<222> LOCATION: (442)
<220> FEATURE:
<221> NAME/KEY: unsure
<222> LOCATION: (461)
<220> FEATURE:
<221> NAME/KEY: unsure
<222> LOCATION: (476)
<220> FEATURE:
<221> NAME/KEY: unsure
<222> LOCATION: (489)
<220> FEATURE:
<221> NAME/KEY: unsure
<222> LOCATION: (493)

<400> SEQUENCE: 3

```
attccancaa cacaaaaatg ccacaatttg tagaaaaaac cgatctttt cgagtaggtt      60
acgctttacc taaagaaag atcgaagctt tcatggtcga atcattcatc aactacgcta    120
aagaacgaaa aatcgatttc atcccaatcg atgtttcaaa accactaacc gaacaaggnc    180
cattcaattg cataattcac aagatgtatg gccaagaatg gaaccaaaat ctcgaaagtt    240
tcactatcaa caaccctaac gccaccgtta tcgaccaacc aacctccatc caacgcctcc    300
ataaccgaat ctcgatgctt gaacccgtta cccaactcaa catccccaaa ctcaacatac    360
caaaccaact tttaggtcaa gatttcggtt gntttaattc ggtcncaaca ataaaaggac    420
ttaatttttc ctggtgatcg gngaaacgct attaagcggg ntgggaccac gaaggnacac    480
gatatgtcng ttng                                                      494
```

<210> SEQ ID NO 4
<211> LENGTH: 112
<212> TYPE: PRT
<213> ORGANISM: Dimorphotheca sinuata

<400> SEQUENCE: 4

```
Met Pro Gln Phe Val Glu Lys Thr Asp Leu Phe Arg Val Gly Tyr Ala
 1               5                  10                  15
Leu Pro Lys Arg Lys Ile Glu Ala Phe Met Val Glu Ser Phe Ile Asn
            20                  25                  30
Tyr Ala Lys Glu Arg Lys Ile Asp Phe Ile Pro Ile Asp Val Ser Lys
        35                  40                  45
Pro Leu Thr Glu Gln Gly Pro Phe Asn Cys Ile Ile His Lys Met Tyr
    50                  55                  60
Gly Gln Glu Trp Asn Gln Asn Leu Glu Ser Phe Thr Ile Asn Asn Pro
 65                  70                  75                  80
Asn Ala Thr Val Ile Asp Gln Pro Thr Ser Ile Gln Arg Leu His Asn
                85                  90                  95
Arg Ile Ser Met Leu Glu Pro Val Thr Gln Leu Asn Ile Pro Lys Leu
            100                 105                 110
```

<210> SEQ ID NO 5
<211> LENGTH: 1136
<212> TYPE: DNA
<213> ORGANISM: Catalpa speciosa

<400> SEQUENCE: 5

```
gcacgagcca aatgttacag ttcttgatcc tccagatgcc atacagcatg tccacaaccg     60
tcagtctatg cttcaggatg ttgctgacct gaatctgtca gattcatatg aacagttgg    120
tgttcctaaa caattggtta taaaaaatga tccaacatct attcctgatg cagtgaacaa    180
ggctgggctg aggctaccta tggtggcaaa gccattggtt gctaagtcac atgagctgtc    240
tcttgcctat gatgagttct ccctccagaa tcttgaaccc ccacttgttc tgcaggaatt    300
tattaatcac ggaggagtac tcttcaaagt ttatattgtt ggggaagcaa taaaggtggt    360
caggcgtttc tccttgcctg atgtgagtaa gcgtgaacta tcaaagaatg ccggtgttta    420
tcgctttcca gagtatcttg tgctgctgc atctgctgat gaagcagact ggatccttg     480
tgtagctgag ctccctcctc gcccattact tgagaaactg ctaggaatc tacgtcatcg    540
gctgggtctt cgactattca acttggatgt gattcgtgag cacggaactc gagaccacta    600
ctatgttata gatattaact actttccagg atacgggaaa atgccagaat atgagcatat    660
attcaccgat ttcctcttga gccttgttca aagcaaatag aaaagtgtaa tcccggcaag    720
agagtggcag aaggatttga gtgccccat gctcgacaag aagttgtact ccaaaacaaa    780
atcacgcaac aggaaagaat gaagccagtc ctgtgataag ttttgatga ttattgaagg    840
acaaagaatg caaagatcg attcgtttgt tctcatcctt ggcaaaaatt gtcatttaga    900
aggtcctctt ggaagaaggt tcaaattatc cttctgggaa ggcggttttt tttgttcata    960
ttttttgatt ttcgtttcat ttttctcatt tttttgctg gttttcaagt tggtatgctc   1020
ttgatatata ttttgacatt gttagtactc agttgttgcc agtacattct atatttacgg   1080
cctttttgtt ctcaaaaaaa aaaaaaaaa aactcgaggg ggggccgta cacaat         1136
```

<210> SEQ ID NO 6
<211> LENGTH: 232
<212> TYPE: PRT
<213> ORGANISM: Catalpa speciosa

<400> SEQUENCE: 6

His Glu Pro Asn Val Thr Val Leu Asp Pro Pro Asp Ala Ile Gln His

```
                1               5              10              15
            Val His Asn Arg Gln Ser Met Leu Gln Asp Val Ala Asp Leu Asn Leu
                           20                  25                  30

Ser Asp Ser Tyr Gly Thr Val Gly Val Pro Lys Gln Leu Val Ile Lys
                           35                  40                  45

Asn Asp Pro Thr Ser Ile Pro Asp Ala Val Asn Lys Ala Gly Leu Arg
                           50                  55                  60

Leu Pro Met Val Ala Lys Pro Leu Val Ala Lys Ser His Glu Leu Ser
             65                70                  75                  80

Leu Ala Tyr Asp Glu Phe Ser Leu Gln Asn Leu Glu Pro Pro Leu Val
                           85                  90                  95

Leu Gln Glu Phe Ile Asn His Gly Val Leu Phe Lys Val Tyr Ile
                          100                 105                 110

Val Gly Glu Ala Ile Lys Val Val Arg Arg Phe Ser Leu Pro Asp Val
                          115                 120                 125

Ser Lys Arg Glu Leu Ser Lys Asn Ala Gly Val Tyr Arg Phe Pro Arg
                  130                 135                 140

Val Ser Cys Ala Ala Ser Ala Asp Glu Ala Asp Leu Asp Pro Cys
            145                 150                 155                 160

Val Ala Glu Leu Pro Pro Arg Pro Leu Leu Glu Lys Leu Ala Arg Asn
                          165                 170                 175

Leu Arg His Arg Leu Gly Leu Arg Leu Phe Asn Leu Asp Val Ile Arg
                          180                 185                 190

Glu His Gly Thr Arg Asp His Tyr Tyr Val Ile Asp Ile Asn Tyr Phe
                          195                 200                 205

Pro Gly Tyr Gly Lys Met Pro Glu Tyr Glu His Ile Phe Thr Asp Phe
                   210                 215                 220

Leu Leu Ser Leu Val Gln Ser Lys
            225                 230

<210> SEQ ID NO 7
<211> LENGTH: 1197
<212> TYPE: DNA
<213> ORGANISM: Zea mays
<220> FEATURE:
<221> NAME/KEY: unsure
<222> LOCATION: (311)
<220> FEATURE:
<221> NAME/KEY: unsure
<222> LOCATION: (330)
<220> FEATURE:
<221> NAME/KEY: unsure
<222> LOCATION: (849)..(850)
<220> FEATURE:
<221> NAME/KEY: unsure
<222> LOCATION: (941)
<220> FEATURE:
<221> NAME/KEY: unsure
<222> LOCATION: (1112)
<220> FEATURE:
<221> NAME/KEY: unsure
<222> LOCATION: (1138)
<220> FEATURE:
<221> NAME/KEY: unsure
<222> LOCATION: (1156)
<220> FEATURE:
<221> NAME/KEY: unsure
<222> LOCATION: (1190)

<400> SEQUENCE: 7
gcaaatttca atctccatcg atcgattcct cccgaacccg acccgatggc ctccgacgcc    60
gccgccgagc cctcctccgg cgtcacccac ccccgcgct acgtcatcgg ttacgcgctc    120
```

-continued

```
gcgccgaaga agcagcaaag cttcatccag ccgtcgctgg tggcccaggc ggcgtcgcgg      180
ggcatggacc tcgtccccgt ggatgcgtcg cagcccctgg cagagcaagg gcccttccac      240
ctcctcatcc acaagctcta cggagacgac tggcgcgccc agctcgtggc cttcgccgcg      300
cgccaaccgg ncgtcccatc gtcgacccgn ccacgccatc gaccgctcca caaccgcatc      360
tccatgctcc aggtcgtctc cgagctcgac acgccgtcg accaggacag cactttcggt       420
atccccagcc aggtcgtcgt ctacgacgct gccgcgctcg ccgacttcgg actccttgcc      480
gcgctccgct tcccgctcat cgccaagccc tcgtcgccg acggcaccgc caagtcccac       540
aagatgtcgc tcgtctacca ccgcgagggc ctcggcaagc tccgcccgcc gcttgtgctc      600
caggagttcg tcaaccatgg cggcgtcatc ttcaaggtct acgtcgtcgg cggccacgtc      660
acttgcgtca agcgccgtag cctgcccgac gtgtccccg aggatgacgc atcggcccag       720
ggatccgtct ccttctccca ggtctccaac ctccccactg agcgcacggc ggaggagtac      780
tacggcgaaa agagtctcga ggacgccgtc gtgccgcccg ccgcattcat caaccagatc      840
gcgggcggnn ctccgcgcgc gctgggcctg caactcttca acttcgacat gatccgcgac      900
gtccgcgccg gcgaccgcta tctcgtcatt gacatcaacc ntacttcggg ctacgccaag      960
atgccaggat acgagactgt ctacggatttt cttctgggag atggtccata aggacggcgt     1020
gggcaaccaa caggaggaag aaagggggcca accattgttg tcgggaaata agaatgatga     1080
attgatggca acttgggata attcttgggc cnaaaatggc ttggcttgga aattcctngg      1140
gaatggccaa gaaaanttcc gaattggaaa gggggggaaa tttttaaaan tttgggg        1197
```

<210> SEQ ID NO 8
<211> LENGTH: 321
<212> TYPE: PRT
<213> ORGANISM: Zea mays
<220> FEATURE:
<221> NAME/KEY: UNSURE
<222> LOCATION: (89)
<220> FEATURE:
<221> NAME/KEY: UNSURE
<222> LOCATION: (269)
<220> FEATURE:
<221> NAME/KEY: UNSURE
<222> LOCATION: (299)

<400> SEQUENCE: 8

```
Met Ala Ser Asp Ala Ala Glu Pro Ser Gly Val Thr His Pro
  1               5                  10                  15

Pro Arg Tyr Val Ile Gly Tyr Ala Leu Ala Pro Lys Lys Gln Gln Ser
                 20                  25                  30

Phe Ile Gln Pro Ser Leu Val Ala Gln Ala Ala Ser Arg Gly Met Asp
             35                  40                  45

Leu Val Pro Val Asp Ala Ser Gln Pro Leu Ala Glu Gln Gly Pro Phe
         50                  55                  60

His Leu Leu Ile His Lys Leu Tyr Gly Asp Asp Trp Arg Ala Gln Leu
 65                  70                  75                  80

Val Ala Phe Ala Ala Arg Gln Pro Xaa Val Pro Ser Ser Thr Arg Pro
                 85                  90                  95

Arg His Arg Pro Leu His Asn Arg Ile Ser Met Leu Gln Val Val Ser
                100                 105                 110

Glu Leu Asp His Ala Val Asp Gln Asp Ser Thr Phe Gly Ile Pro Ser
            115                 120                 125

Gln Val Val Val Tyr Asp Ala Ala Ala Leu Ala Asp Phe Gly Leu Leu
```

|  | 130 |  |  |  | 135 |  |  |  | 140 |  |  |  |  |  |
|---|---|---|---|---|---|---|---|---|---|---|---|---|---|---|

Ala Ala Leu Arg Phe Pro Leu Ile Ala Lys Pro Leu Val Ala Asp Gly
145                 150                 155                 160

Thr Ala Lys Ser His Lys Met Ser Leu Val Tyr His Arg Glu Gly Leu
                165                 170                 175

Gly Lys Leu Arg Pro Pro Leu Val Leu Gln Glu Phe Val Asn His Gly
            180                 185                 190

Gly Val Ile Phe Lys Val Tyr Val Gly Gly His Val Thr Cys Val
        195                 200                 205

Lys Arg Arg Ser Leu Pro Asp Val Ser Pro Glu Asp Ala Ser Ala
210                 215                 220

Gln Gly Ser Val Ser Phe Ser Gln Val Ser Asn Leu Pro Thr Glu Arg
225                 230                 235                 240

Thr Ala Glu Glu Tyr Tyr Gly Glu Lys Ser Leu Glu Asp Ala Val Val
                245                 250                 255

Pro Pro Ala Ala Phe Ile Asn Gln Ile Ala Gly Gly Xaa Pro Arg Ala
            260                 265                 270

Leu Gly Leu Gln Leu Phe Asn Phe Asp Met Ile Arg Asp Val Arg Ala
        275                 280                 285

Gly Asp Arg Tyr Leu Val Ile Asp Ile Asn Xaa Thr Ser Gly Tyr Ala
    290                 295                 300

Lys Met Pro Gly Tyr Glu Thr Val Tyr Gly Phe Leu Leu Gly Asp Gly
305                 310                 315                 320

Pro

<210> SEQ ID NO 9
<211> LENGTH: 518
<212> TYPE: DNA
<213> ORGANISM: Oryza sativa
<220> FEATURE:
<221> NAME/KEY: unsure
<222> LOCATION: (366)
<220> FEATURE:
<221> NAME/KEY: unsure
<222> LOCATION: (391)
<220> FEATURE:
<221> NAME/KEY: unsure
<222> LOCATION: (431)
<220> FEATURE:
<221> NAME/KEY: unsure
<222> LOCATION: (438)
<220> FEATURE:
<221> NAME/KEY: unsure
<222> LOCATION: (447)
<220> FEATURE:
<221> NAME/KEY: unsure
<222> LOCATION: (463)
<220> FEATURE:
<221> NAME/KEY: unsure
<222> LOCATION: (500)
<220> FEATURE:
<221> NAME/KEY: unsure
<222> LOCATION: (509)

<400> SEQUENCE: 9
ggaacaccca gaagttactg ttcttgaccc accaggtgcc atagaacatc tgcttaatcg      60
tcaatctatg cttcaagagg tttctgaatt ggacctctca gattgtcatg gtagagtcgg     120
tgttcctaag cagctgtttg ttaatacaga tccatcatca ataccagctg ctgttatgag     180
ggctggtcta tctcttccat tagtggcaaa gcctctggtg gcaaaatccc atgagttatc     240
tcttgcttat gatccaatct ccttgacgaa gcttgagcct ccgcttgttc ttcaggaatt     300

```
tgtaaaccat ggtggtgtct tgtttaaggt ctacattgtt ggggatgcca tacgggttgt    360
gcgtangttt tcgcttccca acgttgatgt nggtgattta tcaaacaatg ctggagtatt    420
ccggtttcaa nggtctcntg tgctcangca aaccagatat ganattgggc cccatgttct    480
gaactcccca agacactccn agatattgna agagagtg                           518
```

<210> SEQ ID NO 10
<211> LENGTH: 244
<212> TYPE: PRT
<213> ORGANISM: Oryza sativa

<400> SEQUENCE: 10

```
Glu His Pro Glu Val Thr Val Leu Asp Pro Pro Gly Ala Ile Glu His
  1               5                  10                  15

Leu Leu Asn Arg Gln Ser Met Leu Gln Val Ser Glu Leu Asp Leu
                 20                  25                  30

Ser Asp Cys His Gly Arg Val Gly Val Pro Lys Gln Leu Phe Val Asn
             35                  40                  45

Thr Asp Pro Ser Ser Ile Pro Ala Ala Val Met Arg Ala Gly Leu Ser
         50                  55                  60

Leu Pro Leu Val Ala Lys Pro Leu Val Ala Lys Ser His Glu Leu Ser
 65                  70                  75                  80

Leu Ala Tyr Asp Pro Ile Ser Leu Thr Lys Leu Glu Pro Pro Leu Val
                 85                  90                  95

Leu Gln Glu Phe Val Asn His Gly Gly Val Leu Phe Lys Val Tyr Ile
            100                 105                 110

Val Gly Asp Ala Ile Arg Val Val Arg Arg Phe Ser Leu Pro Asn Val
        115                 120                 125

Asp Val Gly Asp Leu Ser Asn Asn Ala Gly Val Phe Arg Phe Pro Arg
    130                 135                 140

Val Ser Cys Ala Ser Ala Asn Ala Asp Asp Ala Asp Leu Asp Pro His
145                 150                 155                 160

Val Ala Glu Leu Pro Pro Arg Pro Leu Leu Glu Ile Leu Ala Arg Glu
                165                 170                 175

Leu Arg Arg Arg Leu Gly Leu Arg Leu Phe Asn Ile Asp Met Ile Arg
            180                 185                 190

Glu His Gly Thr Arg Asp Arg Phe Tyr Val Ile Asp Met Asn Tyr Phe
        195                 200                 205

Pro Gly Tyr Gly Lys Met Pro Gly Tyr Glu His Val Phe Thr Asp Phe
    210                 215                 220

Leu Leu Ser Leu Val Gln Lys Glu Tyr Lys Arg Arg Pro Ser Tyr Ser
225                 230                 235                 240

Ser Cys Glu Gly
```

<210> SEQ ID NO 11
<211> LENGTH: 1574
<212> TYPE: DNA
<213> ORGANISM: Oryza sativa

<400> SEQUENCE: 11

```
gcacgaggaa gagggaaatc gcgtgggcga ggaggaggga ggagagagag ccgcttccgc     60
ttgattcgat tcgaagcaaa accaacccaa cccaacccaa ctcaaccgaa tcgatggccg    120
gcgacgagcc cctccccggc gacgggcagc ggcggcgcta cctcatcggc tacgccctgg    180
cgccgaagaa gcagcagagc ttcatccagc cgtcgctggt gtcgcgcgcg gcggggcgcg    240
```

-continued

```
gcatggacct cgtccccgtc gacccctcgc ggcccctccc cgagcagggg cccttccacc    300
tcctcatcca caagctctac ggcgaggagt ggcgcggtca gctggacgcc ttctccgccg    360
cgcacccagc cgtccccgtc gtcgacccgc cccacgccat cgaccgcctc cacaaccgca    420
tctccatgct ccaggtcgtc tccgagctcg acgtcccgct ccacgccac caccaccaca    480
ccttcggcat cccctcccag gtcgtcgtct acgacgccgc cgccctctcc gactccggcc    540
tcctcgccgc cctccgcttc cccctcatcg ccaagccccc cgtcgccgac ggcaccgcca    600
agtcccacaa gatgtccctc gtctaccacc gcgagggcct ccgcaagctc cgccccccgc    660
tcgtcctcca ggagttcgtc aaccacgcgc gcgtcatctt caaggtctac gtcgtcggcg    720
cccacgtcac ctgcgtcaag cgccgcagcc tccccgacgt ctccagcgac gtcctccagg    780
acgcctccgg cgagggctcc ctctccttct cccaggtctc caacctcccc aacgaggcgc    840
acgcccagga gtactacgac gacatgcgcc tcgaggacgc catcatgcca cccaccgctt    900
tcacaaagaa cttggccgcc ggcctcgcgc gcctgggcct tccactcttc aaatttgaca    960
tgatccggga cccccccgct gggaatcgct acctcgtcat tgacatcaat tacttccccg   1020
gctatgccaa gatgcccgga tacgagactg tgctcaccga tttcttctgg gagatggttc   1080
acaaggacga cgacacgccc aacctcaacc ccaaccccaa tgacgaggat gtcaaatgag   1140
ccacatcaat ttcgactgcc atgctcgcaa acgtgcaatg cctggatgtc agcgcgaggt   1200
accaggtatg ctggttgcag aaaatctgat gagggggaata acgagcaagc aattaggatg   1260
gggagatcgg gattaacgga ttcctgacca tgtcgggggtt tcaccggtgc catgcacaga   1320
ccctacctgc ggtgtaaatc ctttctccta actcctttca tactggttgt tttaggtatc   1380
cttctgttct tcgtaatttg cttcatctag tttagttaga gcagccaaga gagagaaaag   1440
aaatgaagaa cgaagttctc aaagaaaatt tgctcggtgc aaaaaaaaaa aaaaaaaaa    1500
aaaaaaaaaa aaaaaaaaaa aaaaaaaaaa aaaaaaaaa aaaaaaaac tcgagggggg    1560
ggccggtaca catt                                                     1574
```

<210> SEQ ID NO 12
<211> LENGTH: 341
<212> TYPE: PRT
<213> ORGANISM: Oryza sativa

<400> SEQUENCE: 12

```
Met Ala Gly Asp Glu Pro Leu Pro Gly Asp Gly Gln Arg Arg Tyr
  1               5                  10                  15

Leu Ile Gly Tyr Ala Leu Ala Pro Lys Lys Gln Gln Ser Phe Ile Gln
             20                  25                  30

Pro Ser Leu Val Ser Arg Ala Ala Gly Arg Gly Met Asp Leu Val Pro
         35                  40                  45

Val Asp Pro Ser Arg Pro Leu Pro Glu Gln Gly Pro Phe His Leu Leu
     50                  55                  60

Ile His Lys Leu Tyr Gly Glu Glu Trp Arg Gly Gln Leu Asp Ala Phe
 65                  70                  75                  80

Ser Ala Ala His Pro Ala Val Pro Val Val Asp Pro Pro His Ala Ile
                 85                  90                  95

Asp Arg Leu His Asn Arg Ile Ser Met Leu Gln Val Val Ser Glu Leu
            100                 105                 110

Asp Val Pro Leu His Ala His His His Thr Phe Gly Ile Pro Ser
        115                 120                 125

Gln Val Val Val Tyr Asp Ala Ala Ala Leu Ser Asp Ser Gly Leu Leu
```

-continued

```
                 130                 135                 140
Ala Ala Leu Arg Phe Pro Leu Ile Ala Lys Pro Leu Val Ala Asp Gly
145                 150                 155                 160

Thr Ala Lys Ser His Lys Met Ser Leu Val Tyr His Arg Glu Gly Leu
                165                 170                 175

Arg Lys Leu Arg Pro Pro Leu Val Leu Gln Glu Phe Val Asn His Gly
            180                 185                 190

Gly Val Ile Phe Lys Val Tyr Val Gly Ala His Val Thr Cys Val
        195                 200                 205

Lys Arg Arg Ser Leu Pro Asp Val Ser Ser Asp Val Leu Gln Asp Ala
210                 215                 220

Ser Gly Glu Gly Ser Leu Ser Phe Ser Gln Val Ser Asn Leu Pro Asn
225                 230                 235                 240

Glu Ala His Ala Gln Glu Tyr Tyr Asp Asp Met Arg Leu Glu Asp Ala
                245                 250                 255

Ile Met Pro Pro Thr Ala Phe Thr Lys Asn Leu Ala Ala Gly Leu Ala
            260                 265                 270

Arg Leu Gly Leu Pro Leu Phe Lys Phe Asp Met Ile Arg Asp Pro Pro
        275                 280                 285

Ala Gly Asn Arg Tyr Leu Val Ile Asp Ile Asn Tyr Phe Pro Gly Tyr
    290                 295                 300

Ala Lys Met Pro Gly Tyr Glu Thr Val Leu Thr Asp Phe Phe Trp Glu
305                 310                 315                 320

Met Val His Lys Asp Asp Thr Pro Asn Leu Asn Pro Asn Pro Asn
                325                 330                 335

Asp Glu Asp Val Lys
            340

<210> SEQ ID NO 13
<211> LENGTH: 511
<212> TYPE: DNA
<213> ORGANISM: Oryza sativa

<400> SEQUENCE: 13
cagctggtca ctaccaacaa gtacaacaca caagtcatca catatatata cctcgcatcg      60
catcgattcc atcgattcgc gcggccatgg cgcccgagct gtcctcccg tcgtcgtcac      120 ctcgctacac cgttggctac gcgctgctgc cggagaaggt gagcagcgtc gtgcggccgt      180
cgctggtggc gctggccgcc gaccgcgggt gcgcctcgt cgccgtcgac gtgtcgcggc      240
cgctcgccga gcagggcccg ttcgacctcc tcgtgcacaa gatgtacgac gcgggtggc      300 gcgcccagct ggaggagctc gccgcgcgcc accccgggt gaccgtcgtc gtcgactccc      360
ccggcgccat cgaccgcctc ctcgaccgcg ccaccatgct cgacgtcgtc tccgggctcc      420
gcaaccccgt ctccgtccgg ccccaggtcg tcgtcagcga cgccgccgcg acgcggacga      480
gctccctcgc cgcgcgcgct ccgcttctcg g                                      511

<210> SEQ ID NO 14
<211> LENGTH: 141
<212> TYPE: PRT
<213> ORGANISM: Oryza sativa

<400> SEQUENCE: 14

Met Ala Pro Glu Leu Ser Ser Pro Ser Ser Pro Arg Tyr Thr Val
 1               5                  10                  15

Gly Tyr Ala Leu Leu Pro Glu Lys Val Ser Ser Val Val Arg Pro Ser
```

```
                    20                  25                  30
Leu Val Ala Leu Ala Ala Asp Arg Gly Val Arg Leu Val Ala Val Asp
        35                  40                  45
Val Ser Arg Pro Leu Ala Glu Gln Gly Pro Phe Asp Leu Leu Val His
    50                  55                  60
Lys Met Tyr Asp Arg Gly Trp Arg Ala Gln Leu Glu Glu Leu Ala Ala
65                  70                  75                  80
Arg His Pro Gly Val Thr Val Val Asp Ser Pro Gly Ala Ile Asp
                85                  90                  95
Arg Leu Leu Asp Arg Ala Thr Met Leu Asp Val Val Ser Gly Leu Arg
            100                 105                 110
Asn Pro Val Ser Val Arg Pro Gln Val Val Val Ser Asp Ala Ala Ala
        115                 120                 125
Thr Arg Thr Ser Ser Leu Ala Ala Arg Ala Pro Leu Leu
    130                 135                 140

<210> SEQ ID NO 15
<211> LENGTH: 1802
<212> TYPE: DNA
<213> ORGANISM: Glycine max

<400> SEQUENCE: 15
aacgcaatta atgtgagtta gctcactcat taggcacccc aggctttaca ctttatgctt     60
ccggctcgta tgttgtgtgg aattgtgagc ggataacaat ttcacacagg aaacagctat    120
gaccatgatt acgccaagcg cgcaattaac cctcactaaa gggaacaaaa gctggagctc    180
caccgcggtg cggccgctc tagaactagt ggatccccg gctgcagga attcggcacg    240 agccctagtc taagctatat atatccccac tccgttccct atttcccttc tgtccttcct    300 tttctctcc ctcactcatc cgttccgttg ttcagaata ttcatcacca tcgggcccag    360
caccaaaccc cttcccctct cccccaaatt agggtttctc tctgggaatg tgattcagcg    420
cgcggcagca tcaatggcgg agaagagatt cggcgtgata gggtacgctc tggcgccgaa    480
gaagcagaac agcttcatcc gcgactcgct ggtgagccta cgaaatcgc gagggattga    540 gctcgtgcgc gtggactccg acaagcccct cgcggatcag gccccttcg actgcgtcct    600 ccacaagctc tacggcgacg actggaagcg ccagctccag gaattccaca ccctctaccc    660
aaacgccgtc atcctcgacg ccccgaggc gatcgagcgc tccacaaccc gaatctcgat    720
gctgcaggtc gtgtcggagc tccgaattga ggaccgaccc gagaccttg ggatccccaa    780 gcagattgtg atatacgaca aggccacccct cctggacccg caggcctggg agagcctcaa    840
gtttcccgtg atagcgaagc ctctcgttgc cgacggcagc gccaagtcgc acaagatggc    900
gctcgtgttc acgcgcgacg cactgaacaa gctcaagccg ccgatcgtgc tgcaggagtt    960
cgtgaaccac ggtggcgtga tcttcaaggt gtacgtggtg ggcgagcacg tgcgctgcgt   1020
gaagcgcaag tccctccccg acgtgtccga cgaggagaag gcgctcggcg gcgtttccga   1080
ggacctgatg tcgttctcgc aggtctccaa cctcgccacc gtgaacgact gcgacggcta   1140
ttaccgtttg atgcatctcg acgacgacac cgaaatgccc cccgacgcct cgtcgtcga   1200 catcgctggg ggcctcaggc gcgccctcaa gctcaacctc ttcaatttcg atgtcataag   1260
agacgctcga tacgggaacc gttatcttat cattgatatc aactatttcc ctgggtacgc   1320
caaaatgccc ggctacgagg ccgttttgac ccagttttc tgcgaagtaa tgctcaagaa   1380
gaaacagcaa gaggaacaac agcaagaaga gggtaacgct cctaaggaga agaggaatc   1440
```

-continued

```
tcttcaagct tgagataatt ttgtcacaca gatgttgttc tgtcggtgtc ggtgtttggt    1500
ggttttgggg taacccgaat ttccccagtg gacccattgg ttggcacgag ttgcaaattt    1560
cgatttaggg tgcagttggt acagtagggt tgtttgtggc tagttttttt taaccctctt    1620
caacaacatg tatattcctt tcaccattgc tctctggaga taggtacctt ttcaaatacc    1680
ctcaacattt aggaaagttg tattttgcgg cttaagatta ccaagctaga aactgtttac    1740
tttgtgtttt ttttactcaa taacttcatt tttcccattt tgccaaaaaa aaaaaaaaaa    1800
aa                                                                   1802
```

<210> SEQ ID NO 16
<211> LENGTH: 399
<212> TYPE: PRT
<213> ORGANISM: Glycine max

<400> SEQUENCE: 16

```
Ala Ile Tyr Ile Pro Thr Pro Phe Pro Ile Ser Leu Leu Ser Phe Leu
  1               5                  10                  15

Phe Leu Ser Leu Thr His Pro Phe Arg Trp Phe Arg Ile Phe Ile Thr
             20                  25                  30

Ile Gly Pro Ser Thr Lys Pro Leu Pro Leu Ser Pro Lys Leu Gly Phe
         35                  40                  45

Leu Ser Gly Asn Val Ile Gln Arg Ala Ala Ser Met Ala Glu Lys
     50                  55                  60

Arg Phe Gly Val Ile Gly Tyr Ala Leu Ala Pro Lys Lys Gln Asn Ser
 65                  70                  75                  80

Phe Ile Arg Asp Ser Leu Val Ser Leu Ala Lys Ser Arg Gly Ile Glu
                 85                  90                  95

Leu Val Arg Val Asp Ser Asp Lys Pro Leu Ala Asp Gln Gly Pro Phe
            100                 105                 110

Asp Cys Val Leu His Lys Leu Tyr Gly Asp Asp Trp Lys Arg Gln Leu
        115                 120                 125

Gln Glu Phe His Thr Leu Tyr Pro Asn Ala Val Ile Leu Asp Ala Pro
    130                 135                 140

Glu Ala Ile Glu Arg Leu His Asn Arg Ile Ser Met Leu Gln Val Val
145                 150                 155                 160

Ser Glu Leu Arg Ile Glu Asp Arg Pro Glu Thr Phe Gly Ile Pro Lys
                165                 170                 175

Gln Ile Val Ile Tyr Asp Lys Ala Thr Leu Leu Asp Pro Gln Ala Trp
            180                 185                 190

Glu Ser Leu Lys Phe Pro Val Ile Ala Lys Pro Leu Val Ala Asp Gly
        195                 200                 205

Ser Ala Lys Ser His Lys Met Ala Leu Val Phe Thr Arg Asp Ala Leu
    210                 215                 220

Asn Lys Leu Lys Pro Pro Ile Val Leu Gln Glu Phe Val Asn His Gly
225                 230                 235                 240

Gly Val Ile Phe Lys Val Tyr Val Val Gly Glu His Val Arg Cys Val
                245                 250                 255

Lys Arg Lys Ser Leu Pro Asp Val Ser Asp Glu Glu Lys Ala Leu Gly
            260                 265                 270

Gly Val Ser Glu Asp Leu Met Ser Phe Ser Gln Val Ser Asn Leu Ala
        275                 280                 285

Thr Val Asn Asp Cys Asp Gly Tyr Tyr Arg Leu Met His Leu Asp Asp
    290                 295                 300
```

```
Asp Thr Glu Met Pro Pro Asp Ala Phe Val Val Asp Ile Ala Gly Gly
305                 310                 315                 320
Leu Arg Arg Ala Leu Lys Leu Asn Leu Phe Asn Phe Asp Val Ile Arg
            325                 330                 335
Asp Ala Arg Tyr Gly Asn Arg Tyr Leu Ile Ile Asp Ile Asn Tyr Phe
                340                 345                 350
Pro Gly Tyr Ala Lys Met Pro Gly Tyr Glu Ala Val Leu Thr Gln Phe
            355                 360                 365
Phe Cys Glu Val Met Leu Lys Lys Lys Gln Gln Glu Gln Gln Gln
        370                 375                 380
Glu Glu Gly Asn Ala Pro Lys Glu Lys Glu Glu Ser Leu Gln Ala
385                 390                 395
```

<210> SEQ ID NO 17
<211> LENGTH: 1306
<212> TYPE: DNA
<213> ORGANISM: Glycine max

<400> SEQUENCE: 17

```
ctcttcctct tcccacaaat cgtgacacat ttctctcttt cccttctcta ttccgcgcga    60
ttcgcaaact cccagattga acccgcccg cgcgcaaatt gaagaagaga aggccaaaag   120
atttgatctt tcaatcgagg ggtttctggg gtgtccgagg atgaggctca acggtgaaat   180
ctcaagtgga gaagaagagg agaaacaaac gggaacgacg acgttttcgt cgcagaaagt   240
ggtcgttggc tacgctttaa cgtccaagaa gaaaagagc tttctgcagc caagtttcac   300
tggcctcgca cggaacaggg ggataaactt tgttgctatt gatctaaaca agccactgct   360
agaacaaggt ccttttgata ttatcttgca taagttgtca ggggaggagt ggtgtgagat   420
tattgaggat tataggcaaa acatccaga ggtaactgtc cttgatcctc cggatgcaat   480
ccaacattta cacaatcgcc aatccatgct gcaagatgtg gtggatctga acttatctga   540
ttgtcatggc aaggttggtg ttccacgtca gctagttatc ccaaaagaga aagacccctc   600
tagtatccct tacgaaatca ctaaggctgg gatgaagttg ccattagttg caaaaccact   660
agttgtggat ggcactgcaa agtcacatga actatttctt gcttatgatg aattctctct   720
ttcagagctt gaacctccac tagttctaca gagtttgtc aatcatggtg gtcttctctt   780
taagatttac attgttgggg aaaccataaa ggttgtgaag cgtttctctc ttcctaacat   840
cagtaagcat gaggtatcaa agttgctgg tgtattccgt tttccaagag tttcatgtgc   900
agccgcttct gcagatgatg ctgatttaga tcctaatatc gctgaacatc cgccaagacc   960
tttattggag aggcttgcga gggagctccg ccatcgattg ggactgtgct tgttcaacat  1020
agatatgatt cgagaatatg gaaccaagga tgtgttttac gtcattgaca tcaactactt  1080
tcccggatat ggaaaaatgc cagactatga gcacgtattt acagattttc tacttagcct  1140
agtgcagagc aattgtaaga gaaacttgc tacctaaact agagcaagtt ttagtagatc  1200
agatccattg agcagggctg ttcttgctgg tggctttctt aataatttat gcaaactact  1260
ctggaatttc aatgaagcca ccaaaatgtt gaaaaaaaa aaaaaa                  1306
```

<210> SEQ ID NO 18
<211> LENGTH: 338
<212> TYPE: PRT
<213> ORGANISM: Glycine max

<400> SEQUENCE: 18

Met Arg Leu Asn Gly Glu Ile Ser Ser Gly Glu Glu Glu Glu Lys Gln

```
               1               5              10              15
            Thr Gly Thr Thr Thr Phe Ser Ser Gln Lys Val Val Gly Tyr Ala
                            20                  25                  30

Leu Thr Ser Lys Lys Lys Ser Phe Leu Gln Pro Ser Phe Thr Gly
                            35                  40                  45

Leu Ala Arg Asn Arg Gly Ile Asn Phe Val Ala Ile Asp Leu Asn Lys
                            50                  55                  60

Pro Leu Leu Glu Gln Gly Pro Phe Asp Ile Ile Leu His Lys Leu Ser
             65                  70                  75                  80

Gly Glu Glu Trp Cys Glu Ile Ile Glu Asp Tyr Arg Gln Lys His Pro
                            85                  90                  95

Glu Val Thr Val Leu Asp Pro Asp Ala Ile Gln His Leu His Asn
                            100                 105                 110

Arg Gln Ser Met Leu Gln Asp Val Val Asp Leu Asn Leu Ser Asp Cys
                            115                 120                 125

His Gly Lys Val Gly Val Pro Arg Gln Leu Val Ile Pro Lys Glu Lys
                        130                 135                 140

Asp Pro Ser Ser Ile Pro Tyr Glu Ile Thr Lys Ala Gly Met Lys Leu
            145                 150                 155                 160

Pro Leu Val Ala Lys Pro Leu Val Asp Gly Thr Ala Lys Ser His
                            165                 170                 175

Glu Leu Phe Leu Ala Tyr Asp Glu Phe Ser Leu Ser Glu Leu Glu Pro
                            180                 185                 190

Pro Leu Val Leu Gln Glu Phe Val Asn His Gly Leu Leu Phe Lys
                        195                 200                 205

Ile Tyr Ile Val Gly Glu Thr Ile Lys Val Val Lys Arg Phe Ser Leu
                        210                 215                 220

Pro Asn Ile Ser Lys His Glu Val Ser Lys Val Ala Gly Val Phe Arg
            225                 230                 235                 240

Phe Pro Arg Val Ser Cys Ala Ala Ser Ala Asp Asp Ala Asp Leu
                            245                 250                 255

Asp Pro Asn Ile Ala Glu His Pro Pro Arg Pro Leu Leu Glu Arg Leu
                            260                 265                 270

Ala Arg Glu Leu Arg His Arg Leu Gly Leu Cys Leu Phe Asn Ile Asp
                            275                 280                 285

Met Ile Arg Glu Tyr Gly Thr Lys Asp Val Phe Tyr Val Ile Asp Ile
                            290                 295                 300

Asn Tyr Phe Pro Gly Tyr Gly Lys Met Pro Asp Tyr Glu His Val Phe
            305                 310                 315                 320

Thr Asp Phe Leu Leu Ser Leu Val Gln Ser Asn Cys Lys Lys Lys Leu
                            325                 330                 335

Ala Thr
```

<210> SEQ ID NO 19
<211> LENGTH: 910
<212> TYPE: DNA
<213> ORGANISM: Glycine max

<400> SEQUENCE: 19

```
ttcttttcaa ggtttatata gttggtgatg ctataaaggt cgttaggcgg ttttcattac      60
ctgatgtaag caagtgggaa ctctcgaaag atgctgggat atatcgtttt ccaagggttt     120
cttgtgctgc agcttctgca gatgatgctg atttggatcc tactgttgct gagcttcctc     180
caagaccttt actagagaaa ctggctaagg aacttcgatg gcgattgggt cttcgtctat     240
```

```
tcaacctgga tattatccgt gagtatggaa caagaaatca cttttacgtc attgacataa    300
actacttccc tggatatggc aaaatgccag aatatgaaca tatatttaca gacttcctgt    360
tgagcttggg gcaggggaag tacaagaaaa aataggctaa aataactgtt tccagcccct    420
ttatttatgt cccccacatg acgtaagccc ccttgcctct cagtttgaag ctcaaaacta    480
tggctgtagg aaagtatctt agaaagcatt agtgataata acttttttcag ttatgctgtg    540 tgatggaagt gccatggaaa actatcaaga cttgtgtttc aggaacttcg acctgtacag    600
aacaactgct agtattttat tgtgcgggaa ctttcggctg tccttccaag gtaacaaatg    660
ctgttgcaaa tcctctgaag ttctataagc tggtagcttg atgaacgaag gggtcaagtc    720
tgcaatttga aggatttgtc ttcgcaccgc agtggatgtt aatatgaccg tgttggataa    780
gttgacggat ttcaaatgta ctgacccgtt ctttgctgta tataaggcat aaattcttct    840
cgcctcgtgc cttttgcgct ggtatggata gtcaatgtgt tcgtgagcgc cacggtgacg    900
atagaagtgt                                                           910
```

```
<210> SEQ ID NO 20
<211> LENGTH: 130
<212> TYPE: PRT
<213> ORGANISM: Glycine max

<400> SEQUENCE: 20
```

```
Leu Phe Lys Val Tyr Ile Val Gly Asp Ala Ile Lys Val Val Arg Arg
  1               5                  10                  15

Phe Ser Leu Pro Asp Val Ser Lys Trp Glu Leu Ser Lys Asp Ala Gly
             20                  25                  30

Ile Tyr Arg Phe Pro Arg Val Ser Cys Ala Ala Ser Ala Asp Asp
         35                  40                  45

Ala Asp Leu Asp Pro Thr Val Ala Glu Leu Pro Pro Arg Pro Leu Leu
     50                  55                  60

Glu Lys Leu Ala Lys Glu Leu Arg Trp Arg Leu Gly Leu Arg Leu Phe
 65                  70                  75                  80

Asn Leu Asp Ile Ile Arg Glu Tyr Gly Thr Arg Asn His Phe Tyr Val
                 85                  90                  95

Ile Asp Ile Asn Tyr Phe Pro Gly Tyr Gly Lys Met Pro Glu Tyr Glu
            100                 105                 110

His Ile Phe Thr Asp Phe Leu Leu Ser Leu Gly Gln Gly Lys Tyr Lys
        115                 120                 125

Lys Lys
    130
```

```
<210> SEQ ID NO 21
<211> LENGTH: 1040
<212> TYPE: DNA
<213> ORGANISM: Glycine max

<400> SEQUENCE: 21
```

```
gcaccaggca ggtcagaggt accgtgtggg ctatgctctc caaggcaaga aagtcgaaag     60
cttcattcaa ccctcactcc tcgatcacgc caaacaacac agcatcgatc tcgtccaaat    120 cgacccacc gcaccttac aacaacaagg tcctttccac tgcatcattc acaaactcca    180
cacccaacac tggaaaaacc tcctccaaca attctcatcc aaacacccaa acaccgtaat    240
catcgaccct cccgagctgg tggatcgcct gcacaaccgg gtttcaatgc tcgacgcagt    300 gaccccactta caattttccc tcgaaaacgc caccattggg gttccaaagc aagtggttgt    360
```

```
gaacgaaccc aaatccttcg atttgcacaa attcgaagaa gaacagggct tgcggttccc      420
ggtgattgcg aaaccgctgg cggctgacgg cggcgccggc tctcacgaac tgtgtttggt      480
tttcgacgag gagggactcc acgcgttgag cgttcccatg gtgctgcaag agttcgtgaa      540
tcacggcggg gtcgtgttca agatttacgt tgctgggcag cgcgtgaatt gcgtaaagcg      600
caagtctttg ggtgacataa cggaagagaa gctgaaagtg ttaagggggt cgctgccgtt      660
ttctcgtgtg tcgagtttgg gggttgaaga cgagggtggc ggcgccgttg aggacgctga      720
aatgcctccg cagagtttgg tgggtgagtt ggcgagggga ttgagggagg cattgggact      780 taacctttt aacgttgatg tcattagaga tggtaaggaa ccgacaaggt acctcgttat       840
tgatatcaat tactttcccg ggtatgcgaa attgccctct tatgagcctt ttatcaccga      900 tttttgttg gacattgtac gctccaagac tgcgtagtgc gtaggcaaat agttgaaagt      960
ccgaggatga tcgatgatgt tattacacat ttacactgtt gtctaatcat ttttgttatg     1020
ctgttttaaa aaaaaaaaa                                                   1040
```

<210> SEQ ID NO 22
<211> LENGTH: 313
<212> TYPE: PRT
<213> ORGANISM: Glycine max

<400> SEQUENCE: 22

```
Ile Arg His Gln Ala Gly Gln Arg Tyr Arg Val Gly Tyr Ala Leu Gln
  1               5                  10                  15

Gly Lys Lys Val Glu Ser Phe Ile Gln Pro Ser Leu Leu Asp His Ala
             20                  25                  30

Lys Gln His Ser Ile Asp Leu Val Gln Ile Asp Pro Thr Ala Pro Leu
         35                  40                  45

Gln Gln Gln Gly Pro Phe His Cys Ile Ile His Lys Leu His Thr Gln
     50                  55                  60

His Trp Lys Asn Leu Leu Gln Gln Phe Ser Ser Lys His Pro Asn Thr
 65                  70                  75                  80

Val Ile Ile Asp Pro Pro Glu Leu Val Asp Arg Leu His Asn Arg Val
                 85                  90                  95

Ser Met Leu Asp Ala Val Thr His Leu Gln Phe Ser Leu Glu Asn Ala
            100                 105                 110

Thr Ile Gly Val Pro Lys Gln Val Val Asn Glu Pro Lys Ser Phe
        115                 120                 125

Asp Leu His Lys Phe Glu Glu Glu Gln Gly Leu Arg Phe Pro Val Ile
    130                 135                 140

Ala Lys Pro Leu Ala Ala Asp Gly Gly Ala Gly Ser His Glu Leu Cys
145                 150                 155                 160

Leu Val Phe Asp Glu Glu Gly Leu His Ala Leu Ser Val Pro Met Val
                165                 170                 175

Leu Gln Glu Phe Val Asn His Gly Val Val Phe Lys Ile Tyr Val
            180                 185                 190

Ala Gly Gln Arg Val Asn Cys Val Lys Arg Lys Ser Leu Gly Asp Ile
        195                 200                 205

Thr Glu Glu Lys Leu Lys Val Leu Arg Gly Ser Leu Pro Phe Ser Arg
    210                 215                 220

Val Ser Ser Leu Gly Val Glu Asp Glu Gly Gly Gly Ala Val Glu Asp
225                 230                 235                 240

Ala Glu Met Pro Pro Gln Ser Leu Val Gly Glu Leu Ala Arg Gly Leu
```

```
                        245                 250                 255
Arg Glu Ala Leu Gly Leu Asn Leu Phe Asn Val Asp Val Ile Arg Asp
                260                 265                 270
Gly Lys Glu Pro Thr Arg Tyr Leu Val Ile Asp Ile Asn Tyr Phe Pro
            275                 280                 285
Gly Tyr Ala Lys Leu Pro Ser Tyr Glu Pro Phe Ile Thr Asp Phe Leu
        290                 295                 300
Leu Asp Ile Val Arg Ser Lys Thr Ala
305                 310

<210> SEQ ID NO 23
<211> LENGTH: 522
<212> TYPE: DNA
<213> ORGANISM: Triticum aestivum

<400> SEQUENCE: 23
gcacgaggcc aagcagagtc gagcgagcga tcaaatcatg gtggccgacc acccagtcct      60
ccccgcggcc gcgggtcacc atcggctacg cgctgccgcc cggcaaggcg ggcagcgtca     120
tccagccgcc gcttgaggcc ctcgcggcgg agcgcggcat gcgcctcgtc gccgtcgacg     180
cctcgctgcc cctggccgac cagggcccct tcgacctcat catccacaag ctcttcgacc     240
ggccctggcg cgcgcagctg gaggccttct ccgcgctcca cccctccgtg cccgtcgtcg     300 acgccccgc cgccgtcgac cgcctgctcg accgcttcac catgctcgac gtcgtccccg     360
ggctcgccgc cggcctggac ttcccgctca gcgtccccgc gcaagtcacc gtgaagcgac     420
gccgccgcgc tggccgcgga cgacccgtcc cacgggctcc gctcccgctc atcgccaagc     480
cgctggccgt cgacggagcg caactccaag actggctgtg tt                       522

<210> SEQ ID NO 24
<211> LENGTH: 160
<212> TYPE: PRT
<213> ORGANISM: Triticum aestivum

<400> SEQUENCE: 24

Met Val Ala Asp His Gln Ser Ser Pro Arg Pro Arg Val Thr Ile Gly
  1               5                  10                  15
Tyr Ala Leu Pro Pro Gly Lys Ala Gly Ser Val Ile Gln Pro Pro Leu
             20                  25                  30
Glu Ala Leu Ala Ala Glu Arg Gly Met Arg Leu Val Ala Val Asp Ala
         35                  40                  45
Ser Leu Pro Leu Ala Asp Gln Gly Pro Phe Asp Leu Ile Ile His Lys
     50                  55                  60
Leu Phe Asp Arg Pro Trp Arg Ala Gln Leu Glu Ala Phe Ser Ala Leu
 65                  70                  75                  80
His Pro Ser Val Pro Val Asp Ala Pro Ala Val Asp Arg Leu
                 85                  90                  95
Leu Asp Arg Phe Thr Met Leu Asp Val Val Pro Gly Leu Ala Ala Gly
                100                 105                 110
Leu Asp Phe Pro Leu Ser Val Pro Ala Gln Val Thr Val Lys Arg Arg
            115                 120                 125
Arg Arg Ala Gly Arg Gly Arg Pro Ser Thr Gly Ser Leu Pro Leu Ile
        130                 135                 140
Ala Lys Pro Leu Ala Ser Thr Glu Arg Asn Ser Lys Thr Gly Cys Val
145                 150                 155                 160
```

<210> SEQ ID NO 25
<211> LENGTH: 511
<212> TYPE: DNA
<213> ORGANISM: Triticum aestivum

<400> SEQUENCE: 25

```
cggccgcgcc gtctgcgtcc gccgcagcag cttgccggac gtgcccgcgg aggcgcctcg      60
cggaccccga cgcggacgcc tccgtcccct tcgccaacat ctccagccgc ccgcgctgg      120
acaaggggga ggactcgatg ccgccgccg cgttcgtgga ccaggtggcg cgcgggctcc      180
ggcaggcgct ggggctgcac ctcctcaact tcgacatgtt cgcggcgacg gagctggacg      240
acggcggccg gcggaggtac ttcctcgtgg acatcaacta cttcccgggg ttcgccaaga      300
tgccgggcta cgagactgct ctcacggatt tcttcgccga gatgattcag ctaggcactg      360
caggcgccgc cgccggccaa gagaagctcg aatctgtgcc ctgcaatgag ctctaggaaa      420
ctgggtttac tttggacttt tgatgaacag ggtgtcccta ctgccgagaa taaaaattaa      480
gaacgctttg cggcgtaaaa aaaaaaaaaa a                                    511
```

<210> SEQ ID NO 26
<211> LENGTH: 105
<212> TYPE: PRT
<213> ORGANISM: Triticum aestivum

<400> SEQUENCE: 26

```
Ile Ser Ser Arg Pro Ala Leu Asp Lys Gly Glu Asp Ser Met Pro Pro
  1               5                  10                  15
Ala Ala Phe Val Asp Gln Val Ala Arg Gly Leu Arg Gln Ala Leu Gly
             20                  25                  30
Leu His Leu Leu Asn Phe Asp Met Phe Ala Ala Thr Glu Leu Asp Asp
         35                  40                  45
Gly Gly Arg Arg Arg Tyr Phe Leu Val Asp Ile Asn Tyr Phe Pro Gly
     50                  55                  60
Phe Ala Lys Met Pro Gly Tyr Glu Thr Ala Leu Thr Asp Phe Phe Ala
 65                  70                  75                  80
Glu Met Ile Gln Leu Gly Thr Ala Gly Ala Ala Gly Gln Glu Lys
                 85                  90                  95
Leu Glu Ser Val Pro Cys Asn Glu Leu
            100                 105
```

<210> SEQ ID NO 27
<211> LENGTH: 505
<212> TYPE: DNA
<213> ORGANISM: Triticum aestivum

<400> SEQUENCE: 27

```
gcacgaggat caaggcccct tttgatgttat tctgcataag ttgactggaa aggagtggca      60
acgacggttg gaggaatata gagacacaca cccagaagtt actgttcttg acccaccagg     120
tgccatagaa catttgctga accgccaatc tatgcttcaa gaagtttcta actggacct      180
tgcggattgt catggtaaag ttggtgttcc gaagcagctt tttgttaaca cagacccatt     240
gtcaatacca gctgcggtta tgagggctgg gctatcgctt ccattagtgg cgaagcctct     300
ggtggcgaag tctcatgagt tgtctcttgc ttatgactca gcttccttga cgaagcttga     360
gcctccgttg ttcttcagg aatttgttaa ccatggcggc gtcttattta aggtctacat     420
tgttggggat gcaattaggg tagtgcgtag gttttcactg cctaacgtgg atgacggtga     480
cctgtcaaat aacgccggag tgttc                                          505
```

<210> SEQ ID NO 28
<211> LENGTH: 159
<212> TYPE: PRT
<213> ORGANISM: Triticum aestivum

<400> SEQUENCE: 28

```
His Glu Asp Gln Gly Pro Phe Asp Val Ile Leu His Lys Leu Thr Gly
  1               5                  10                  15

Lys Glu Trp Gln Arg Arg Leu Glu Glu Tyr Arg Asp Thr His Pro Glu
             20                  25                  30

Val Thr Val Leu Asp Pro Pro Gly Ala Ile Glu His Leu Leu Asn Arg
         35                  40                  45

Gln Ser Met Leu Gln Glu Val Ser Lys Leu Asp Leu Ala Asp Cys His
     50                  55                  60

Gly Lys Val Gly Val Pro Lys Gln Leu Phe Val Asn Thr Asp Pro Leu
 65                  70                  75                  80

Ser Ile Pro Ala Ala Val Met Arg Ala Gly Leu Ser Leu Pro Leu Val
                 85                  90                  95

Ala Lys Pro Leu Val Ala Lys Ser His Glu Leu Ser Leu Ala Tyr Asp
            100                 105                 110

Ser Ala Ser Leu Thr Lys Leu Glu Pro Pro Leu Val Leu Gln Glu Phe
        115                 120                 125

Val Asn His Gly Gly Val Leu Phe Lys Val Tyr Ile Val Gly Asp Ala
    130                 135                 140

Ile Arg Val Val Arg Arg Phe Ser Leu Pro Asn Val Asp Asp Gly
145                 150                 155
```

<210> SEQ ID NO 29
<211> LENGTH: 638
<212> TYPE: DNA
<213> ORGANISM: Triticum aestivum

<400> SEQUENCE: 29

```
ccggatcagg tagtggcaac attggctgcg ccgccgactg ggtcttagac tgttcatcat      60
atctatgatc agagagcatg ggacacggga tcggttttat gttatagaca tgaactattt     120
tcctgggtat gggaagatgc ctggatacga gcatgttttc accgacttcc tgctgagcct     180
agaccagcag aaggagtaca agcgacgact gggctatacg tcgggtgagg ggtgaagagt     240
cgaggccgac caacttccct ctgacctttg ccagtatgtt gtctcttcgc attcgctgtg     300
tgtacgaatg aatgtgcata tcaggagggg aaggatcatc aagtttcatc tgtggtagag     360
ttgggcatca gtagttgcga tgataaggca gcgaggactg tgttgaactg taattattaa     420
tccgcatttt ggggcaactg tgttctcttc atgttcttga ataatctcgt tcggcctagc     480
aatggaatcg agcgggtatc cgcacccaca tcaggtgtcc cagaaatctc aaagttatgt     540
agaacaatcc acgcaatatt tccctgctga cgtgtggttg tgcactggcg gaggtcttgg     600
ctaaaaaaaa aaaaaaaaaa aaaaaaaaaa aaaaaaa                              638
```

<210> SEQ ID NO 30
<211> LENGTH: 67
<212> TYPE: PRT
<213> ORGANISM: Triticum aestivum

<400> SEQUENCE: 30

```
Arg Arg Leu Gly Leu Arg Leu Phe Ile Ile Ser Met Ile Arg Glu His
  1               5                  10                  15
```

Gly Thr Arg Asp Arg Phe Tyr Val Ile Asp Met Asn Tyr Phe Pro Gly
             20                  25                  30

Tyr Gly Lys Met Pro Gly Tyr Glu His Val Phe Thr Asp Phe Leu Leu
         35                  40                  45

Ser Leu Asp Gln Gln Lys Glu Tyr Lys Arg Arg Leu Gly Tyr Thr Ser
     50                  55                  60

Gly Glu Gly
 65

<210> SEQ ID NO 31
<211> LENGTH: 1141
<212> TYPE: DNA
<213> ORGANISM: Triticum aestivum

<400> SEQUENCE: 31
tttcatacca attgatgaga ctcgtcctct ctccgaacaa ggcccatttg atattatctt      60
gcacaagaaa actagcaagg agtggcagcg gtttctggag gattatcatg aagtgcatcc     120
agaagtcact gtcctcgacc cacccaatgc cattgagcat ctgaacaatc gacaatcgat     180
gcttgaagaa gtagcagatt tgaacctgtc cagtttctat gaagaagttt gcactccacg     240
ccaactggtc attatgaaag atccgtcctc tataccaact gcagttgcca tggctgggct     300
aaccttgcca ttggttgcca agccattggt tgttgatgga acatctaaat ctcatgagct     360
atctctggca tacgatgagg cgtccttgcc aatgcttgat cctcctctgg tactccaaga     420
atttgtgaat catgggggg atctctttaa ggtgtacatc attggtgaag ctatacaggt     480
tgtccgcagg ttttctcttc ctgatgttaa acccttggcc ttactaaaca attgttgcat     540
cttttggactt ccagggtttt cttgcgttgc agcaagttcc gatcatgcag cccttgatcc     600
tcgtattgca gagcttcccc cgagaccact tctagagaaa ctaggcaggg agcgtcgtgg     660
tcgtctgggt ctaagattgt tcaacataga tatgattaga gagcttggag caaatgaccg     720
gtactatata attgatatca actacttccc aggatatggg aaaatgcctg gctatgagca     780
catattcacc gatttcttgc aaagtcttgg gcaaaacaaa taccaaaggt gcttgagcgg     840
aggctgaagc gctggtagcc atacttgttc actaatgtgc atatcttgga tacataagct     900
ggagcccaag gcttgaagtc ccaaacttac atgttttgtc agaaatggcg ccacatacac     960
agggtcggga gtagggggag agaaagaaga actcgaatgg ccttgtgccc atcttgtata    1020
aatcacggtt gttttgatca tagtttggtc tcaaatgctt tcatcaaaca ggatcagcac    1080
catcaaccca ccatgtatgt ggctcgaggg ggggcccgta cacaatcaaa ccctgggggc    1140
c                                                                   1141

<210> SEQ ID NO 32
<211> LENGTH: 281
<212> TYPE: PRT
<213> ORGANISM: Triticum aestivum

<400> SEQUENCE: 32

Phe Ile Pro Ile Asp Glu Thr Arg Pro Leu Ser Glu Gln Gly Pro Phe
  1               5                  10                  15

Asp Ile Ile Leu His Lys Lys Thr Ser Lys Glu Trp Gln Arg Phe Leu
             20                  25                  30

Glu Asp Tyr His Glu Val His Pro Glu Val Thr Val Leu Asp Pro Pro
         35                  40                  45

Asn Ala Ile Glu His Leu Asn Asn Arg Gln Ser Met Leu Glu Glu Val

```
                50                      55                      60
Ala Asp Leu Asn Leu Ser Ser Phe Tyr Glu Glu Val Cys Thr Pro Arg
 65                      70                      75                  80

Gln Leu Val Ile Met Lys Asp Pro Ser Ile Pro Thr Ala Val Ala
                    85                      90                  95

Met Ala Gly Leu Thr Leu Pro Leu Val Ala Lys Pro Leu Val Val Asp
                100                     105                     110

Gly Thr Ser Lys Ser His Glu Leu Ser Leu Ala Tyr Asp Glu Ala Ser
                115                     120                     125

Leu Pro Met Leu Asp Pro Pro Leu Val Leu Gln Glu Phe Val Asn His
130                     135                     140

Gly Gly Asp Leu Phe Lys Val Tyr Ile Ile Gly Glu Ala Ile Gln Val
145                     150                     155                 160

Val Arg Arg Phe Ser Leu Pro Asp Val Lys Pro Leu Ala Leu Leu Asn
                165                     170                     175

Asn Cys Cys Ile Phe Gly Leu Pro Gly Val Ser Cys Val Ala Ala Ser
                180                     185                     190

Ser Asp His Ala Ala Leu Asp Pro Arg Ile Ala Glu Leu Pro Pro Arg
                195                     200                     205

Pro Leu Leu Glu Lys Leu Gly Arg Glu Arg Gly Arg Leu Gly Leu
                210                     215                     220

Arg Leu Phe Asn Ile Asp Met Ile Arg Glu Leu Gly Ala Asn Asp Arg
225                     230                     235                 240

Tyr Tyr Ile Ile Asp Ile Asn Tyr Phe Pro Gly Tyr Gly Lys Met Pro
                245                     250                     255

Gly Tyr Glu His Ile Phe Thr Asp Phe Leu Gln Ser Leu Gly Gln Asn
                260                     265                     270

Lys Tyr Gln Arg Cys Leu Ser Gly Gly
                275                     280

<210> SEQ ID NO 33
<211> LENGTH: 319
<212> TYPE: PRT
<213> ORGANISM: Arabidopsis thaliana

<400> SEQUENCE: 33

Met Ser Asp Ser Ile Gln Glu Arg Tyr Leu Val Gly Tyr Ala Leu Ala
 1                       5                      10                  15

Ala Lys Lys Gln His Ser Phe Ile Gln Pro Ser Leu Ile Glu His Ser
                    20                      25                  30

Arg Gln Arg Gly Ile Asp Leu Val Lys Leu Asp Pro Thr Lys Ser Leu
                35                      40                      45

Leu Glu Gln Gly Lys Leu Asp Cys Ile Ile His Lys Leu Tyr Asp Val
     50                      55                      60

Tyr Trp Lys Glu Asn Leu His Glu Phe Arg Glu Lys Cys Pro Gly Val
 65                      70                      75                  80

Pro Val Ile Asp Leu Pro Glu Ala Ile Glu Arg Leu His Asn Arg Val
                    85                      90                  95

Ser Met Leu Glu Val Ile Thr Gln Leu Arg Phe Pro Val Ser Asp Ser
                100                     105                     110

Glu Arg Phe Gly Val Pro Glu Gln Val Val Met Asp Ser Ser Val
                115                     120                     125

Leu Ser Gly Gly Ala Leu Gly Glu Leu Lys Phe Pro Val Ile Ala
                130                     135                     140
```

```
Lys Pro Leu Asp Ala Asp Gly Ser Ala Lys Ser His Lys Met Phe Leu
145                 150                 155                 160

Ile Tyr Asp Gln Glu Gly Met Lys Ile Leu Lys Ala Pro Ile Val Leu
                165                 170                 175

Gln Glu Phe Val Asn His Gly Val Ile Phe Lys Val Tyr Val Val
            180                 185                 190

Gly Asp His Val Gln Cys Val Lys Arg Arg Ser Leu Pro Asp Ile Ser
            195                 200                 205

Glu Glu Lys Ile Gly Thr Ser Lys Gly Ser Leu Pro Phe Ser Gln Ile
            210                 215                 220

Ser Asn Leu Thr Ala Gln Asp Lys Asn Ile Glu Tyr Gly Glu Asp
225                 230                 235                 240

Arg Ser Leu Glu Lys Val Glu Met Pro Pro Leu Ser Phe Leu Thr Asp
                245                 250                 255

Leu Ala Lys Ala Met Arg Glu Ser Met Gly Leu Asn Leu Phe Asn Phe
            260                 265                 270

Asp Val Ile Arg Asp Ala Lys Asp Ala Asn Arg Tyr Leu Ile Ile Asp
            275                 280                 285

Ile Asn Tyr Phe Pro Gly Tyr Ala Lys Met Pro Ser Tyr Glu Pro Val
290                 295                 300

Leu Thr Glu Phe Phe Trp Asp Met Val Thr Lys Lys Asn His Val
305                 310                 315

<210> SEQ ID NO 34
<211> LENGTH: 319
<212> TYPE: PRT
<213> ORGANISM: Arabidopsis thaliana

<400> SEQUENCE: 34

Met Ser Asp Ser Ile Gln Glu Arg Tyr Leu Val Gly Tyr Ala Leu Ala
1               5                   10                  15

Ala Lys Lys Gln His Ser Phe Ile Gln Pro Ser Leu Ile Glu His Ser
                20                  25                  30

Arg Gln Arg Gly Ile Asp Leu Val Lys Leu Asp Pro Thr Lys Ser Leu
            35                  40                  45

Leu Glu Gln Gly Lys Leu Asp Cys Ile Ile His Lys Leu Tyr Asp Val
50                  55                  60

Tyr Trp Lys Glu Asn Leu His Glu Phe Arg Glu Lys Cys Pro Gly Val
65                  70                  75                  80

Pro Val Ile Asp Leu Pro Glu Ala Ile Glu Arg Leu His Asn Arg Val
                85                  90                  95

Ser Met Leu Glu Val Ile Thr Gln Leu Arg Phe Pro Val Ser Asp Ser
            100                 105                 110

Glu Arg Phe Gly Val Pro Glu Gln Val Val Met Asp Ser Ser Val
            115                 120                 125

Leu Ser Gly Gly Ala Leu Gly Glu Leu Lys Phe Pro Val Ile Ala
            130                 135                 140

Lys Pro Leu Asp Ala Asp Gly Ser Ala Lys Ser His Lys Met Phe Leu
145                 150                 155                 160

Ile Tyr Asp Gln Glu Gly Met Lys Ile Leu Lys Ala Pro Ile Val Leu
                165                 170                 175

Gln Glu Phe Val Asn His Gly Val Ile Phe Lys Val Tyr Val Val
            180                 185                 190

Gly Asp His Val Lys Cys Val Lys Arg Arg Ser Leu Pro Asp Ile Ser
            195                 200                 205
```

-continued

```
Glu Glu Lys Ile Gly Thr Ser Lys Gly Ser Leu Pro Phe Ser Gln Ile
    210             215             220

Ser Asn Leu Thr Ala Gln Glu Asp Lys Asn Ile Glu Tyr Gly Glu Asp
225             230             235             240

Arg Ser Leu Glu Lys Val Glu Met Pro Pro Leu Ser Phe Leu Thr Asp
            245             250             255

Leu Ala Lys Ala Met Arg Glu Ser Met Gly Leu Asn Leu Phe Asn Phe
            260             265             270

Asp Val Ile Arg Asp Ala Lys Asp Ala Asn Arg Tyr Leu Ile Ile Asp
        275             280             285

Ile Asn Tyr Phe Pro Gly Tyr Ala Lys Met Pro Ser Tyr Glu Pro Val
    290             295             300

Leu Thr Glu Phe Phe Trp Asp Met Val Thr Lys Lys Asn His Val
305             310             315
```